United States Patent
Iyer et al.

(10) Patent No.: US 11,242,298 B2
(45) Date of Patent: Feb. 8, 2022

(54) NATURAL GAS PROCESSING AND SYSTEMS

(71) Applicant: Lummus Technology LLC, The Woodlands, TX (US)

(72) Inventors: Rahul Iyer, Kensington, CA (US); Alex Tkachenko, San Francisco, CA (US); Sam Weinberger, San Francisco, CA (US); Erik C. Scher, San Francisco, CA (US); Guido Radaelli, South San Francisco, CA (US); Hatem Harraz, San Francisco, CA (US)

(73) Assignee: Lummus Technology LLC, The Woodlands, TX (US)

( * ) Notice: Subject to any disclaimer, the term of this patent is extended or adjusted under 35 U.S.C. 154(b) by 0 days.

(21) Appl. No.: 16/528,227

(22) Filed: Jul. 31, 2019

(65) Prior Publication Data
US 2020/0354287 A1    Nov. 12, 2020

Related U.S. Application Data

(63) Continuation of application No. 16/213,027, filed on Dec. 7, 2018, now abandoned, which is a continuation (Continued)

(51) Int. Cl.
C07C 2/82    (2006.01)
C07C 2/84    (2006.01)
(Continued)

(52) U.S. Cl.
CPC ........ *C07C 2/82* (2013.01); *B01J 8/02* (2013.01); *B01J 8/04* (2013.01); *C07C 2/06* (2013.01);
(Continued)

(58) Field of Classification Search
None
See application file for complete search history.

(56) References Cited

U.S. PATENT DOCUMENTS

| | | | |
|---|---|---|---|
| 2,324,172 | A | 7/1943 | Parkhurst |
| 2,486,980 | A | 11/1949 | Robinson |

(Continued)

FOREIGN PATENT DOCUMENTS

| | | |
|---|---|---|
| CA | 2041874 C | 4/1999 |
| CA | 2765769 A1 | 1/2011 |

(Continued)

OTHER PUBLICATIONS

Chemical Engineering—"Separation Processes: Supercritical CO2: A Green Solvent" Feb. 1, 2010.
(Continued)

*Primary Examiner* — Ali Z Fadhel
(74) *Attorney, Agent, or Firm* — Calfee, Halter & Griswold LLP

(57) ABSTRACT

The present disclosure provides natural gas and petrochemical processing systems including oxidative coupling of methane reactor systems that integrate process inputs and outputs to cooperatively utilize different inputs and outputs of the various systems in the production of higher hydrocarbons from natural gas and other hydrocarbon feedstocks.

13 Claims, 20 Drawing Sheets

Related U.S. Application Data of application No. 15/950,461, filed on Apr. 11, 2018, now abandoned, which is a continuation of application No. 13/936,870, filed on Jul. 8, 2013, now Pat. No. 9,969,660.

(60) Provisional application No. 61/773,669, filed on Mar. 6, 2013, provisional application No. 61/669,523, filed on Jul. 9, 2012.

(51) Int. Cl.
| | |
|---|---|
| *C07C 2/06* | (2006.01) |
| *B01J 8/02* | (2006.01) |
| *B01J 8/04* | (2006.01) |
| *C10G 50/00* | (2006.01) |
| *C10G 57/00* | (2006.01) |
| *C10G 57/02* | (2006.01) |
| *C10G 9/00* | (2006.01) |

(52) U.S. Cl.
CPC .............. *C07C 2/84* (2013.01); *C10G 9/00* (2013.01); *C10G 50/00* (2013.01); *C10G 57/00* (2013.01); *C10G 57/02* (2013.01); *Y02P 20/52* (2015.11); *Y02P 30/40* (2015.11)

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A | 9/1959 | Ballard et al. |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,516,262 A | 6/1970 | Bernstein |
| 3,584,071 A | 6/1971 | McNulty et al. |
| 3,596,473 A | 8/1971 | Martin |
| 3,660,519 A | 5/1972 | Takaaki et al. |
| 3,686,334 A | 8/1972 | Britton |
| 3,686,350 A | 8/1972 | Isao et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,115,086 A | 9/1978 | Jordan et al. |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Jean et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,418,045 A | 11/1983 | Sato et al. |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,519,824 A | 5/1985 | Huebel |
| 4,523,049 A | 6/1985 | Jones et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,889,545 A | 12/1989 | Campbell et al. |
| 4,891,457 A | 1/1990 | Hartley et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Manfred et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,095,161 A * | 3/1992 | Abrevaya et al. ........ C07C 2/00 585/500 |
| 5,113,032 A | 5/1992 | Cameron et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,245,099 A | 9/1993 | Mitariten |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |

(56) References Cited

U.S. PATENT DOCUMENTS

| | | |
|---|---|---|
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,457,256 A | 10/1995 | Mitariten et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Charles et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A * | 4/1998 | Inomata .................. B01J 8/1863 422/144 |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Trubenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,602,920 B2 * | 8/2003 | Hall .......................... B01J 8/02 518/700 |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassar et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,793,517 B2 | 9/2010 | Patel et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |

(56) References Cited

U.S. PATENT DOCUMENTS

| | | | |
|---|---|---|---|
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1* | 3/2005 | Gattis .............. C10G 50/00 585/324 |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0021379 A1 | 2/2006 | Ronczy |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0194900 A1* | 8/2008 | Bhirud .............. C10G 65/16 585/648 |
| 2008/0207975 A1 | 8/2008 | Crone et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0105066 A1* | 4/2009 | Kang .............. C10G 11/02 502/73 |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Laurilzen et al. |
| 2009/0216059 A1 | 8/2009 | Reyes et al. |

(56) References Cited

U.S. PATENT DOCUMENTS

| | | |
|---|---|---|
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0140144 A1 | 6/2010 | Clinton et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |
| 2010/0222203 A1 | 9/2010 | Baba et al. |
| 2010/0249473 A1* | 9/2010 | Butler .................. C07C 2/82 585/324 |
| 2010/0256245 A1 | 10/2010 | Iaccino et al. |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Neltner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1* | 3/2012 | Abdallah ............. C07C 67/05 549/518 |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2012/0302807 A1 | 11/2012 | Elseviers |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1 | 3/2015 | Henao et al. |
| 2015/0099914 A1 | 4/2015 | Garza et al. |
| 2015/0152025 A1 | 6/2015 | Cizeron et al. |
| 2015/0210610 A1 | 7/2015 | Rafique et al. |
| 2015/0218786 A1 | 8/2015 | Cullen |
| 2015/0232395 A1 | 8/2015 | Nyce et al. |
| 2015/0246856 A1 | 9/2015 | Schmigalle et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Longetai. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washbur et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0022125 A1 | 1/2017 | Fichtl |
| 2017/0057889 A1 | 3/2017 | Sarsani et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0062642 A1* | 2/2019 | Wei .................. B01J 29/48 |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |

(56) References Cited

U.S. PATENT DOCUMENTS

| | | |
|---|---|---|
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |
| 2020/0207685 A1 | 7/2020 | Nyce et al. |
| 2020/0216370 A1 | 7/2020 | Rafique et al. |
| 2020/0231519 A1 | 7/2020 | Abudawoud et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Agarwal, et al., Aqueous Au—Pd colloids catalyze selective CH4 oxidation to CH3OH with O2 under mild conditions, Science 358, Oct. 13, 2017, 223-27.

Ahari, et al. Effects of operating parameters on oxidative coupling of methane over Na—WMn/SiO2 catalyst at elevated pressures. Journal of Natural Gas Chemistry. vol. 20, Issue 2, Mar. 2011, pp. 204-213.

American Petroleum Institute Publication 534 Heat Recovery Steam Generators Jan. 1995 (51 pages).

Autothermal Partial Oxidative Coupling of Methane. IP.com, Prior Art Database Technical Disclosure, Jul. 29, 2008, 5 pages.

Barrett, et al. The determination of pore vol. and area distributions in porous substances—Compuatations from nitrogen isotherms. J. Am. Chem. Soc., 1951, vol. 73, pp. 373-380.

Berstad, D. et al. Low-temperature CO2 removal from natural gas. Energy Procedia (2012) 26:41-48.

Bloch, et al. Hydrocarbon Separations in a Metal-Organic Framework with Open Iron(II) Coordination Sites, Science, 2012, 335:1606-1610.

Bollmann, et al. Ethylene tetramerization: a new route to produce 1-octene in exceptionally high selectivities. J Am Chem Soc. Nov. 17, 2004;126(45):14712-3.

Bottella, et al. Effect of Potassium Doping on the Catalytic Behavior of Mo—V—Sb Mixed Oxide Catalysts in the Oxidation of Propane to Acrylic Acid. Catalysis Letters, Sep. 2003, vol. 89, Issue 3-4, pp. 249-253.

Carter, et al. High activity ethylene trimerisation catalysts based on diphosphine ligands. Chem Commun (Camb). Apr. 21, 2002;(8):858-9.

Caskey, et al., Dramatic Tuning of Carbon Dioxide Uptake via Metal Substitution in a Coordination Polymer with Cylindrical Pores, J. Am. Chem. Soc., (2009), 130(33): 10870-71.

(56) References Cited

OTHER PUBLICATIONS

Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): 15-25, Feb. 2004.
Choudhary, et al. Surface Basicity and Acidity of Alkaline Earth-Promoted La2 O3 Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Corma, From Microporous to Mesoporous Molecular Sieve Materials and Their Use in Catalysis, Chern. Rev., 97, 1997, pp. 2373-2419.
Debart, et al. $\alpha$-MNO2 Nanowires: A catalyst for the O2 Electrode in Rechargeabl Lithium Batteries. Angewandte Chemie International Edition 47: 4521-4524, 2008.
Dietzel, et al., Adsorption properties and structure of CO2 adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Enger, et al. A review of catalytic partial oxidation of methane to synthesis gas with emphasis on reaction mechanisms over transition metal catalysts. Applied Catalysis A: General 346 (1-2): 1-27, Aug. 2008.
Fallah, et al., A New Nano-(2Li2O/MgO) Catalyst/Porous Alpha-Alumina Composite for the Oxidative Coupling of Methane Reaction, AlChE Journal, Mar. 2010, 56(3):717-28.
Gao, et al. A study on methanol steam reforming to COZ and HZ over the LaZ CO4 nanofiber catalyst. Journal of Solid State Chemistry 181: 7-13, 2008.
Gao, et al. The direct decomposition of NO over the La2 CuO4 nanofiber catalyst. Journal of Solid State Chemistry 181: 2804-2807, 2008.
Geier, et al., Selective adsorption of ethylene over ethane and propylene over propane in the metal-organic frameworks M2(dobdc) (M=Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al, Mesoporous Material from Zeolite, Journal of Poruous Materials, 2002, pp. 43-48.
Graves, C.R. Recycling CO2 into Sustainable Hydrocarbon Fuels: Electrolysis of CO2 and H2O. Dissertation, Columbia University (2010).
Guo, et al. Current Status and Some Perspectives of Rare Earth Catalytic Materials. Journal of The Chinese Rare Earth Society 25(1): 1-15, Feb. 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4(4):128-131.
Haag, W.O. et al. Aromatics, Light Olefins and Gasoline from Methanol: Mechanistic Pathways with ZSM-5 Zeolite Catalyst J Mol Catalysis (1982) 17:161-169.
Hosseinpour, Performance of CaX Zeolite for Separation of C2H6, C2H4, and CH4 by Adsorption Process; Capacity, Selectivity, and Dynamic Adsorption Measurements, Separation Science and Technology, 2011, 46:349-355.
Huang, et al. Exploiting shape effects of La2O3 nanocrystals for oxidative coupling of methane reaction. Nanoscale 5(22): 10844-10848, 2013.
Huang, et al. Exploiting shape effects of La2O3 nanocrystals for oxidative coupling of methane reaction. Nanoscale-Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in CO2 capture technology: A patent review. Applied Energy (2013) 102:1439-1447.
Li, et al. Combined Single-Pass Conversion of Methane Via Oxidative Coupling and Dehydroaromatization. Catalysis Letters, Sep. 2003, vol. 89, Issue 3-4, pp. 275-279.
Li, et al. Energy and Fuels. 2008, 22: 1897-1901.
Ling, et al. Preparation of Ag core Au shell Nanowires and Their Surface Enhanced Raman Spectroscopic Studies. Acta Chimica Sinica. 65 (9): 779-784, 2007.
Liu, et al. A novel Na2 WO4-Mn.SiC monolithic foam catalyst with improved thermal properties for the oxidative coupling of methane. Catalysis Communications 9: 1302-1306, 2008.
Liu, et al. Increasing the Density of Adsorbed Hydrogen with Coordinatively Unsaturated Metal Centers in Metal-Organic Frameworks Langmuir, 2008, 24:4772-77.
Lunsford, J.H. Catalytic conversion of methane to more useful chemicals and fuels: a challenge for the 21st century. Catalysis Today (2000) 63:165-174.
Lunsford. The Catalytic Oxidative Coupling of Methane. Angew. Chem Int. Ed. Engl. 1995; 34:970-980.
Lunsford, et al. The oxidative coupling of methane on chlorinated Lithium-doped magnesium oxide. J. Chem. Soc., Chem. Commun., 1991, 1430-1432.
Makal, et al., Methane storage in advanced porous materials, Critical Review, Chem. Soc. Rev., 2012, 41 :7761-7779.
Matherne, et al. Chapter 14, Direct Conversion of Methane to C2's and Liquid Fuels: Process Economics, Methane Conversion by Oxidative Processes (1992), 463-482.
Miltenburg, A.S. Adsorptive Separation of Light Olefin/Paraffin Mixtures: Dispersion of Zeolites. (2007) Ponsen & Looijen B.V., Wageningen, the Netherlands.
Mimoun, H. et al. Oxypyrolysis of Natural Gas. Appl Catalysis (1990) 58:269-280.
Mleczko, et al. Catalytic oxidative coupling of methane—reaction engineering aspects and process schemes. Fuel Processing Technology 42:217-248, 1995.

(56) References Cited

OTHER PUBLICATIONS

Mokhatab et al. "Handbook of Natural Gas Transmission and Processing: Principles and Practices" 2015. Chapter 7, pp. 237-242. (Year: 2015).
Morgan, C.R. et al. Gasoline from Alcohols. Ind Eng Chem Prod Res Dev(1981) 20:185-190.
Natural Gas Spec Sheet, 2003, prepared by Florida Power and Light Company.
Neltner, et al. Production of Hydrogen Using Nanocrystalline Protein-templated catalysts on M12 Phage. ACSNano 4(6):3227-3236, 2010.
Neltner. Hybrid Bio-templated Catalysts. Doctoral Thesis, Massachusetts Institute of Technology, Jun. 2010, 156 pages.
Nexant/Chemsystems HDPE Report, PERP 09/10-3, Jan. 2011.
Nghiem, XS. Ethylene Production by Oxidative Coupling of Methane: New Process Flow Diagram based on Adsorptive Separation. Berlin, Mar. 14, 2014.
Nielsen, et al. Treat LPGs with amines. Hydrocarbon Process 79 (1997): 49-59.
Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.
Niu, et al. Preparation and characterization of La2 O3CO3 nanowires with high surface areas. Jounral of the Chinese Rare Earth Society 23 (Spec. Issue): 33-36, Dec. 2005.
Ogura et al. Formation of Uniform Mesopores in ZSM-5 Zeolite through Treatment in Alkaline Solution, Chemistry Letters, 2000, pp. 882-883.
Ohashi, Y. et al. Development of Carbon Dioxide Removal System from the Flue Gas of Coal Fired Power Plant. Energy Procedia (2011) 4:29-34.
Oil Refinery—Wikipedia, The Free Encyclopedia Website. Jan. 2009.
Olah, G. Hydrocarbon Chemistry. 2nd Edition, John Wiley & Sons, 2003.
Olefins Conversion Technology, Website Accessed Aug. 28, 2014, http:www.CBI.com.
Pak, et al. Elementary Reactions in the Oxidative Coupling of Methane over Mn/NA2 W04/Si02 and MN/NA2 W04/Mg0 Catalysts. Journal of Catalysis 179:222-230, 1998.
Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.
Process Systems; "Steam Tables" Apr. 8, 2017—https://web.archive.org/web/20170408152403/https://valvesonline.com.au/references/steamtables/.
Qiu, et al. Steady-state conversion of methane to aromatics in high yields using an integrated recycle reaction system. Catalysis Letters 48: 11-15, 1997.
Rousseau, Handbook of Separation Process Technology, 1987, p. 682.
Saito, et al. Dehydrogenation of Propane Over a Silica-Supported Gallium Oxide Catalyst. Catalysis Letters, Sep. 2003, vol. 89, Issue 3-4, pp. 213-217.
Schweer, et al. OCM in a fixed bed reactor: limits and perspectives. Catalysis Today, vol. 21, No. 2-3, Dec. 1, 1994, pp. 357-369.
Seeberger, A. et al. Gas Separation by Supported Ionic Liquid Membranes. DGMK—Conference, Hamburg, Germany (2007).
Simons, K. Membrane Technologies For CO2 Capture. Dissertation, U. of Twente (2010).
Smith, et al. Recent developments in solvent absorption technologies at the CO2CRC in Australia. Energy Procedia 1 (2009): 1549-1555.
Somorjai, et al. High technology catalysts towards 100% selectivity Fabrication, characterization and reaction studies. Catalysis today 100:201-215, 2005.

Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.
Suzuki, K. Toshiba's Activity in Clean Coal and Carbon Capture Technology for Thermal Power Plants. APEC Clean Fossil Energy Technical and Policy Seminar (Feb. 22, 2012).
Tabak, S.A. et al. Conversion of Methanol over ZSM-5 to Fuels and Chemicals. Cat Today (1990) 307-327.
Takanabe, et al. Mechanistic Aspects and Reaction Pathways for Oxidative Coupling of Methane on Mn/NA2 W04/Si02 Catalysts. Journal of Physical Chemistry C 113(23):10131-10145, 2009.
Takanabe, et al. Rate and Selectivity Enhancements Mediated by OH Radicals in the Oxidative coupling of Methane Catalyzed by Mn/NA2 W04/SiO2 . Angewandte Chemie International Edition 47:7689-7693, 2008.
Tong, et al. Development strategy research of downstream products of ethene in Tianjin. Tianjin Economy, pp. 37-40,1996.
Trautmann, et al. Cryogenic technology for nitrogen rejection from variable content natural gas. Presented at the XIV Convencion Internacional de Gas, Caracas, Venezuela, May 10-12, 2000, 13 pages.
Wang, et al. Autothermal oxidative coupling of methane on the SrCO3/Sm2 03 catalysts. Catalysis communications 10: 807-810, 2009.
Wang, et al. Comparative study on oxidation of methane to ethane and ethylene over NA2 W04-Mn/SiO2 catalysts prepared by different methods. Journal of Molecular Catalysis A: Chemical 245:272-277, 2006.
Wang, et al. Low temperature selective oxidation of methane to ethane and ethylene over BaCO3/La2 03 catalysts prepared by urea combustion method. Catalysis communications 7: 5963, 2006.
Wang, et al., Critical Influence of BaCO3 on Low Temperature Catalytic Activity of BaCO3/Zr02 Catalysts for Oxidative Coupling of Methane, Catalysis Letters (2009), 129:156-162.
Water Electrolysis & Renewable Energy Systems. FuelCellToday (May 2013).
Wikipedia search, Adiabatic Process, Mar. 2011, 10 pages.
Witek-Krowiak, A. et al. Carbon Dioxide Removal in a Membrane Contactor-Selection of Absorptive Liquid/Membrane System. Intl J Chem Eng and Appl. (2012) 3(6):391-395.
Wong, et al. Oxidative coupling of methane over alkali metal oxide promoted La2 03/BaCO3 catalysts. J. Chem. Tech. Biotechnol. 65:351-354, 1996.
Wu, et al., High-Capacity Methane Storage in Metal-Organic Frameworks M2(dhtp): The Important Role of Open Metal Sites, J. Am. Chem. Soc. 131 (13):4995-5000.
Xu, et al. Maximise ethylene gain and acetylene selective hydrogenation efficiency. Petroleum technology quarterly 18.3 (2013): 39-42.
Xu, G. et al. An Improved CO2 Separation and Purification System Based on Cryogenic Separation and Distillation Theory. Energies (2014) 7:3484-3502.
Yan, D. Modeling and Application of a Thermoelectric Generator. Thesis, Univ. Toronto (2011).
Yang, et al. Anistropic synthesis of boat shaped core shell Au—Ag nanocrystals and nanowires Nanotechnology 17:2304-2310, 2006.
Yu, et al. Oxidative coupling of methane over acceptor-doped SrTi 03: Correlation between p-type conductivity and C2 selectivity and C2 yield. Journal of Catalysis. 13 (5): 338-344, 1992.
Zhang, Q. Journal of Natural Gas Chem., 12:81, 2003.
Zhao, et al. Technologies and catalysts for catalytic preparation of ethene. Industrial catalysis 12 (Supplement): 285-289, 2004.
Zhou, et al. Functionalization of lanthanum hydroxide nanowires by atom transfer radical polymerization. Nanotechnology 18, 2007, 7 pages.
Zhou. BP-UOP Cyclar Process. Handbook of Petroleum Refining Processes, The McGraw-Hill Companies (2004), pp. 2.29-2.38.
Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.

(56) References Cited

OTHER PUBLICATIONS

Zimmerman, et al. Ethylene. Ulmann's Encyclopedia of Inudstrial Chemisty, Wiley-VCH Verlag GmbH & Co. KGaA, Weinheim, Germany, 2009, 66 pages.
Office action dated Nov. 7, 2016 for U.S. Appl. No. 13/936,783.
Office action dated Dec. 23, 2015 for U.S. Appl. No. 13/936,783.
Notice of allowance dated Mar. 15, 2017 for U.S. Appl. No. 13/936,783.
Office action dated Jan. 14, 2016 for U.S. Appl. No. 13/936,870.
Office action dated Mar. 6, 2017 for U.S. Appl. No. 13/936,870.
Office action dated Sep. 6, 2017 for U.S. Appl. No. 13/936,870.
Notice of allowance dated Sep. 22, 2016 for U.S. Appl. No. 13/936,870.
Notice of Allowance dated Mar. 21, 2018 for U.S. Appl. No. 13/936,870.
European search report and search opinion dated Jan. 20, 2016 for EP Application No. 13817389.3.
Examination Report dated Feb. 13, 2019 for EP Application No. 13817389.3.
Notice of Allowance dated Dec. 31, 2019 for Vietnam Patent Application No. 1-2015-00454.
Preliminary Examination Report dated Nov. 19, 2019for Brazil Patent Application No. 1120150003931.
International search report and written opinion dated Nov. 1, 2013 for PCT/US2013/049742.
He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.
Duan, et al. Three-dimensional copper (II) metal-organic framework with open metal sites and anthracene nucleus for highly selective C2H2/CH4 and C2NH2/CO2 gas separation at room temperature. Microporous and Mesoporous Materials. vol. 181, Nov. 15, 2013, pp. 99-104.

\* cited by examiner

NATURAL GAS PROCESSING AND SYSTEMS

CROSS-REFERENCE

This application is a continuation of U.S. patent application Ser. No. 16/213,027, filed Dec. 7, 2018, which is a continuation of U.S. patent application Ser. No. 15/950,461, filed Apr. 11, 2018, which is a continuation of U.S. patent application Ser. No. 13/936,870, filed Jul. 8, 2013, now U.S. Pat. No. 9,969,660, which claims the benefit of U.S. Provisional Patent Application No. 61/773,669, filed Mar. 6, 2013 and U.S. Provisional Patent Application No. 61/669,523, filed Jul. 9, 2012, each of which is incorporated herein by reference in its entirety.

BACKGROUND

There exists an infrastructure for petrochemical processing throughout the world. This infrastructure is deployed on virtually every continent, addresses wide ranging industries, and employs a wide variety of different implementations of similar or widely differing technologies.

As a major constituent to this infrastructure, the gas industry itself involves multiple components from exploration, recovery, processing and conversion technologies in transforming natural gas into useful end products. In the United States alone, the gas industry involves hundreds to thousands of processing and fractionation facilities. These facilities typically include all the requisite process equipment for processing and separating natural gas into its constituent and valued components, as well as the requisite gas delivery infrastructure and storage and distribution infrastructure for a wide range of different products, including liquid products.

Further processing, conversion and/or commercialization of these products may involve still additional infrastructure. For example, conversion of ethane from gas to higher value chemicals, e.g., olefins, involves substantial infrastructure in the form of steam crackers, and their associated infrastructure. Similarly, in other geographies, olefin production relies upon the conversion of petroleum refining by-products, or naphtha, through alternative cracking operations to produce ethylene and other olefins.

As will be appreciated, the capital costs associated with each of the facility types described above can run from tens of millions to hundreds of millions of dollars each. Additionally, there are inputs and outputs, of these facilities, in terms of both energy and materials, which have additional costs associated with them, both financial and otherwise that could be further optimized in terms of cost and efficiency. Further, because different facilities tend to be optimized for the particularities (e.g., products, processing conditions) of the market in which they exist, they tend to be operated in an inflexible manner, in some cases without the flexibility or option to optimize for their given market, e.g., a particular oil or gas environment.

SUMMARY

The present disclosure provides systems and methods for reacting methane in an oxidative coupling of methane ("OCM") process to yield products comprising hydrocarbon compounds with two or more carbon atoms (also "$C_{2+}$ compounds" herein), and separating the products into streams for use in various downstream processes. OCM systems and methods of the disclosure can be integrated in various hydrocarbon processes. The present disclosure provides integrated processing facilities for producing higher hydrocarbons from natural gas and other hydrocarbon feedstocks.

In some examples, processing facilities or systems include an integrated OCM reactor system that provide various components of its OCM product, or other outputs, as an input to various systems in the processing facility, including, for example, refineries, extraction systems, fractionation systems and the like. Alternatively or additionally, integrated OCM reactor systems are provided that take up various product streams or outputs of different units or systems in these processing facilities.

Existing processing infrastructure can be advantageously leveraged for new processing methods and systems without expending significant capital resources in retrofitting that infrastructure, in some cases taking advantage of the different inputs and outputs of these facilities to create much greater value from the same or similar infrastructure, raw materials, and/or process flows.

In an aspect, a method for the oxidative coupling of methane to generate hydrocarbon compounds containing at least two carbon atoms ($C_{2+}$ compounds) comprises (a) directing a feed stream comprising methane from a hydrocarbon process into an oxidative coupling of methane (OCM) reactor, wherein the OCM reactor is configured to generate $C_{2+}$ compounds from the methane, and wherein the hydrocarbon process is a non-OCM process; performing one or more OCM reactions in the OCM reactor using the methane to produce a product stream comprising one or more $C_{2+}$ compounds; and separating the product stream into at least a first stream and a second stream, wherein the first stream has a lower $C_{2+}$ concentration than the second stream, and wherein the second stream has a higher $C_{2+}$ concentration than the product stream.

In some embodiments, the hydrocarbon process is an oil refinery, a natural gas liquids process, or a cracker. In some embodiments, at least a portion of the first stream is directed into the OCM reactor.

In some cases, a concentration of $C_{2+}$ compounds in the second stream is less than about 90%. In some embodiments, concentration of $C_{2+}$ compounds in the second stream is less than about 80%. In some cases, the concentration of $C_{2+}$ compounds in the second stream is less than about 70%. In some embodiments, the concentration of $C_{2+}$ compounds in the second stream is less than about 60%. In some cases, the first stream has a concentration of $C_{2+}$ compounds that is less than about 50%.

In some cases, the product stream is separated in at most three separation units. In some embodiments, the product stream is separated in at most two separations units.

In some cases, the separating is with the aid of pressure swing adsorption. As an alternative, or in addition to, the separating is with the aid of cryogenic separation. As an alternative, or in addition to, the separating is with the aid of temperature swing adsorption.

In another aspect, a method for the oxidative coupling of methane to generate hydrocarbon compounds containing at least two carbon atoms ($C_{2+}$ compounds) comprises (a) directing a feed stream comprising methane into an oxidative coupling of methane (OCM) reactor, wherein the OCM reactor is configured to generate $C_{2+}$ compounds from the methane; (b) performing one or more OCM reactions in the OCM reactor using the methane to produce a product stream comprising one or more $C_{2+}$ compounds; (c) separating the product stream into at least a first stream and a second stream, wherein the first stream has a lower $C_{2+}$ concentration than the second stream, and wherein the second stream has a higher $C_{2+}$ concentration than the product stream; and (d) directing the second stream into a hydrocarbon process, wherein the hydrocarbon process is a non-OCM process.

In some embodiments, the hydrocarbon process is an oil refinery, a natural gas liquids process, or a cracker. In some embodiments, the product stream is separated in at most three separation units.

In some cases, a concentration of $C_{2+}$ compounds in the second stream is within about 20% of a concentration of the $C_{2+}$ compounds in a portion of the hydrocarbon process into which the second stream is directed. In some embodiments, a concentration of $C_{2+}$ compounds in the second stream is within about 5% of a concentration of the $C_{2+}$ compounds in a portion of the hydrocarbon process into which the second stream is directed.

In some cases, the separating is with the aid of pressure swing adsorption. In some embodiments, the separating is with the aid of cryogenic separation. In some embodiments, the feed stream is directed into the OCM reactor with the aid of a pumping system.

In another aspect, an oxidative coupling of methane (OCM) system comprises (a) a non-OCM hydrocarbon process that provides a feed stream comprising methane; (b) an OCM reactor fluidically coupled to the non-OCM hydrocarbon process, wherein the OCM reactor (i) takes as input the feed stream, and (ii) generates, from the methane, a product stream comprising $C_{2+}$ compounds and non-$C_{2+}$ impurities; and (c) at least one separations unit downstream of, and fluidically coupled to, the OCM reactor, wherein the at least one separations unit (i) takes as input the product stream, and (ii) separates the $C_{2+}$ compounds from at least a subset of the non-$C_{2+}$ impurities.

In some cases, the non-OCM hydrocarbon process is an oil refinery, a natural gas liquids process, or a cracker. In some embodiments, the system further comprises a non-OCM hydrocarbon process downstream of the at least one separations unit. In some embodiments, the at least one separations unit comprises a pressure swing adsorption unit. In some embodiments, the at least one separations unit comprises a cryogenic separation unit.

In some embodiments, the non-$C_{2+}$ impurities comprise one or more of nitrogen ($N_2$), oxygen ($O_2$), water ($H_2O$), argon (Ar), carbon monoxide (CO), carbon dioxide ($CO_2$) and methane ($CH_4$).

In another aspect, an oxidative coupling of methane (OCM) system comprises (a) an OCM reactor that (i) takes as input a feed stream comprising methane, and (ii) generates, from the methane, a product stream comprising $C_{2+}$ compounds and non-$C_{2+}$ impurities; (b) at least one separations unit downstream of, and fluidically coupled to, the OCM reactor, wherein the at least one separations unit (i) takes as input the product stream, and (ii) separates the $C_{2+}$ compounds from at least a subset of the non-$C_{2+}$ impurities into a process stream comprising at least a subset of the $C_{2+}$ compounds; and (c) a non-OCM hydrocarbon process downstream of, and fluidically coupled to, the at least one separations unit, wherein the non-OCM hydrocarbon process takes as input the process stream for use in one or more non-OCM processes.

In some embodiments, the non-OCM hydrocarbon process is an oil refinery, a natural gas liquids process, or a cracker. In some embodiments, the system further comprises a non-OCM hydrocarbon process downstream of the at least one separations unit. In some embodiments, the at least one separations unit comprises a pressure swing adsorption unit.

In some cases, the at least one separations unit comprises a cryogenic separation unit.

In another aspect, a method for integrating an oxidative coupling of methane (OCM) process with a hydrocarbon process comprises (a) directing a feed stream comprising methane into an oxidative coupling of methane (OCM) reactor, wherein the OCM reactor is configured to generate $C_{2+}$ compounds from the methane; (b) performing one or more OCM reactions in the OCM reactor using the methane to produce a product stream comprising one or more $C_{2+}$ compounds; (c) separating the product stream into at least a first stream and a second stream, wherein the first stream has a lower $C_{2+}$ concentration than the second stream, and wherein the second stream has a higher $C_{2+}$ concentration than the product stream; and (d) directing the second stream into a process stream of a hydrocarbon process at a point in which the concentration of $C_{2+}$ compounds in the process stream is at most about 10% different than the concentration of $C_{2+}$ compounds in the second stream.

In some cases, the point at which the second stream enters the hydrocarbon process has a concentration of $C_{2+}$ compounds is at most about 5% different than the concentration of the one or more $C_{2+}$ compounds in the second stream. In some embodiments, the concentration of $C_{2+}$ compounds in the second stream is greater than the concentration of the $C_{2+}$ compounds at the point at which the second stream enters the hydrocarbon process.

In some embodiments, the hydrocarbon process is an oil refinery, a natural gas liquids (NGL) process, or a cracker. In some embodiments, the product stream further comprises non-$C_{2+}$ impurities. In some embodiments, the second stream has a lower concentration of the non-$C_{2+}$ impurities than the first stream. In some embodiments, in (d), the second stream is directed into the process stream at a point in which the concentration of $C_{2+}$ compounds is at most about 10% lower than the concentration of $C_{2+}$ compounds in the second stream.

In another aspect, a method for concentrating hydrocarbons having at least two carbon atoms ($C_{2+}$) comprises (a) introducing a fluid comprising one or more $C_{2+}$ compounds and non-$C_{2+}$ impurities into a vessel at a first pressure, wherein the vessel comprises an adsorbent medium, wherein upon introducing the fluid into the vessel, the fluid is brought in contact with the adsorbent medium; (b) changing the pressure in the vessel to a second pressure to release (i) at least a subset of the one or more $C_{2+}$ compounds or (ii) the non-$C_{2+}$ impurities from the adsorbent medium, thereby separating the at least the subset of the one or more $C_{2+}$ compounds from the non-$C_{2+}$ impurities; and (c) recovering the at least the subset of the one or more $C_{2+}$ compounds.

In some embodiments, the one or more $C_{2+}$ compounds are hydrocarbons having between two and five carbon atoms. In some embodiments, the $C_{2+}$ compounds comprise ethylene. In some embodiments, the adsorbent medium is selected from the group consisting of activated carbon, silica gel, alumina and zeolite. In some embodiments, the second pressure is greater than the first pressure. In some embodiments, the second pressure is less than the first pressure.

In another aspect, a method for recovering hydrocarbons having two or more carbon atoms ($C_{2+}$) from an oxidative coupling of methane (OCM) process comprises (a) directing a feed stream comprising methane into an oxidative coupling of methane (OCM) reactor, wherein the OCM reactor is configured to generate $C_{2+}$ compounds from the methane; (b) performing one or more OCM reactions in the OCM reactor using the methane to produce a product stream comprising one or more $C_{2+}$ compounds; (c) subjecting the product stream to pressure swing adsorption (PSA) to generate at least a first stream and a second stream, wherein the first stream has a lower $C_{2+}$ concentration than the second stream.

In some cases, the method further comprises, between (b) and (c), drying the product stream. In some embodiments, subjecting the product stream to PSA separates $C_{2+}$ from methane and impurities. In some cases, the first stream comprises methane and impurities.

In some embodiments, the method further comprises, subsequent to (c), separating the methane from the impurities. In some embodiments, the method further comprises, returning at least a portion of the methane to the OCM reactor. In some embodiments, the impurities comprise argon (Ar), hydrogen ($H_2$), carbon monoxide (CO), carbon dioxide ($CO_2$), nitrogen ($N_2$), or any combination thereof. In some embodiments, at least 95% of the impurities are removed in the PSA.

In another aspect, a method for recovering hydrocarbons having two or more carbon atoms ($C_{2+}$) from an oxidative coupling of methane (OCM) process comprises (a) providing, from an OCM reactor, a product stream comprising $C_{2+}$ compounds, impurities, and methane; (b) separating the product stream to provide at least (i) a first stream enriched in impurities, (ii) a second stream enriched in methane, and (iii) a third stream enriched in $C_{2+}$ compounds; and (c) cooling the third stream to condense the $C_{2+}$ compounds.

In some cases, said first stream has an impurities content of at least about 70%. In some embodiments, the second stream has a methane content of at least about 70%. In some embodiments, the third stream has a $C_{2+}$ content of at least about 70%. In some embodiments, the impurities comprise argon (Ar), hydrogen ($H_2$), carbon monoxide (CO), carbon dioxide ($CO_2$), nitrogen ($N_2$), or any combination thereof.

In some embodiments, the mass flow rate of the third stream is less than 30% of the mass flow rate of the product stream. In some embodiments, the method further comprises flowing the second stream into the reactor. In some embodiments, the method further comprises flowing the third stream into a hydrocarbon process. In some embodiments, the method further comprises flowing a feed stream comprising methane from a hydrocarbon process into the OCM reactor. In some embodiments, the third stream is cooled in a cryogenic separation unit.

In another aspect, a method for integrating an oxidative coupling of methane (OCM) process with a hydrocarbon process comprises (a) providing, from an OCM reactor, a product stream comprising hydrocarbon compounds comprising two or more carbon atoms ($C_{2+}$) and methane; (b) separating the product stream into a first stream enriched in methane and a second stream enriched in $C_{2+}$ compounds; and (c) combusting the methane in the first stream to provide energy for use in a hydrocarbon process.

In some cases, the combusted methane is directed through a heat exchanger that is coupled to a process stream of the hydrocarbon process. In some embodiments, the hydrocarbon process is an oil refinery, a natural gas liquids (NGL) process, or a cracker.

In another aspect, the invention provides natural gas processing systems that comprise an OCM reactor system comprising at least a first reactor vessel having at least a first OCM catalyst disposed therein. The systems also comprise one or more of an extraction system for separating at least one hydrocarbon compound from at least one non-hydrocarbon compound, and a fractionation system for separating at least two different hydrocarbon compounds. The systems further comprise an interconnected pipeline, the interconnected pipeline fluidly connecting one or more of an inlet or an outlet of the OCM reactor system to one or more of an inlet or an outlet of the one or more of the extraction system and the fractionation system.

In another aspect, provided are natural gas processing systems and methods, comprising an OCM reactor system comprising at least a first reactor vessel having at least a first OCM catalyst disposed therein. The system also comprises an extraction system for separating at least one non-hydrocarbon compound from at least one hydrocarbon compound, and a fractionation system for separating at least two different hydrocarbon compounds. Also included is an interconnected pipeline, the interconnected pipeline fluidly connecting one or more of an inlet or an outlet of the OCM reactor system to one or more of an inlet or an outlet of one or more of the fractionation system and the extraction system.

Also provided herein are methods and systems for producing hydrocarbon compounds. The methods comprise contacting methane and air/oxygen with an OCM catalyst under OCM reaction conditions in a first reactor system to produce an OCM product, the OCM product comprising two or more different hydrocarbon compounds. The OCM product produced in the contacting step is then transferred to a fractionation system fluidly coupled to the first reactor system. At least one hydrocarbon compound in the OCM product is then separated from at least one other hydrocarbon compound in the OCM product in the fractionation system.

Another aspect provides methods and systems for producing hydrocarbon compounds, comprising contacting methane and air/oxygen with an OCM catalyst under OCM reaction conditions in a first reactor system to produce an OCM product, the OCM product comprising one or more hydrocarbon compounds and at least one non-hydrocarbon compound. The OCM product produced in the contacting step is transferred to an extraction system fluidly coupled to the first reactor system. At least one hydrocarbon compound in the OCM product is separated from at least one other hydrocarbon or non-hydrocarbon compound in the OCM product.

Also provided herein are integrated hydrocarbon processing systems that include both a steam cracker configured to convert one or more saturated hydrocarbons into one or more unsaturated hydrocarbons, and an OCM reactor system configured to convert methane to ethylene. These two systems are both fluidly connected at their outlets to the inlet of an integrated hydrocarbon fractionation system such that $C_{2+}$ containing streams from each of the steam cracker and OCM reactor system are passed into the fractionation system.

Another aspect provides methods for producing one or more desired hydrocarbon compounds, comprising directing a first hydrocarbon feedstock comprising saturated hydrocarbons to a steam cracker to produce an unsaturated hydrocarbon containing stream. These methods also include directing a second hydrocarbon feedstock comprising methane to an OCM reactor system to produce an ethylene containing stream. The resulting streams, e.g., the unsaturated hydrocarbon containing stream and the ethylene containing stream, are then both directed to an integrated fractionation system, e.g., a common integrated fractionation system, to produce one or more desired hydrocarbon product streams.

Another aspect provides methods and systems for producing hydrocarbon compounds, comprising contacting methane and air/oxygen with an OCM catalyst under OCM reaction conditions in a first reactor system to produce an OCM product, the OCM product comprising one or more different hydrocarbon compounds. The OCM product produced in the contacting step is transferred to an integrated oligomerization system to produce one or more higher hydrocarbon compounds from the one or more hydrocarbon compounds in the OCM product. The one or more higher hydrocarbons produced in the oligomerization system are then transferred to a fractionation system fluidly coupled to the oligomerization system for separating at least one hydrocarbon compound in the OCM product from at least one higher hydrocarbon.

In another aspect, natural gas processing systems and methods comprise an OCM reactor system for processing natural gas to produce an OCM product, the OCM reactor system comprising a thermal energy extraction system thermally coupled to the OCM reactor system for removing thermal energy from the OCM reactor system. The system also includes a natural gas fractionation unit for separating one or more hydrocarbon components in one or more of natural gas or the OCM product from at least one other hydrocarbon product in the natural gas or OCM product. Also included are one or more heat exchangers thermally coupled to each of the thermal energy extraction system and the fractionation unit, to convey thermal energy from the thermal energy extraction system to the fractionation unit to heat the natural gas or OCM product in the fractionation unit to separate the one or more hydrocarbon components in the natural gas or OCM product from at least one other hydrocarbon product in the natural gas or OCM product.

In another aspect, natural gas processing systems and methods comprise an extraction system for separating methane from NGLs in natural gas, the extraction system having a methane rich effluent outlet, and further comprising an OCM reactor system comprising an inlet fluidly coupled to the methane rich effluent outlet of the extraction system. The system also comprises a thermal energy removal system for removing thermal energy from the OCM reactor system, and a heat exchanger thermally coupled to each of the thermal energy removal system and a fluid connection between the methane rich effluent outlet and the OCM reactor inlet, for heating a methane rich effluent from the extraction system to greater than 400° C.

In another aspect, natural gas processing systems and methods comprise an OCM reactor system, a steam generator thermally coupled to the OCM reactor, to generate steam from thermal energy produced by the OCM reactor, and an electrical generator coupled to the steam generator for generating electricity from steam produced by the steam generator.

In another aspect, methods and systems for collecting $CO_2$ comprise, in an OCM reactor system, contacting methane and air/oxygen with an OCM catalyst under OCM reaction conditions to produce a product stream comprising one or more hydrocarbon compounds and $CO_2$, separating $CO_2$ from the one or more hydrocarbon compounds in the product stream in an extraction system integrated with the OCM reactor system, and collecting the $CO_2$ separated from the product stream.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "Fig." and "Figs." herein), of which:

DETAILED DESCRIPTION

Figure 1:
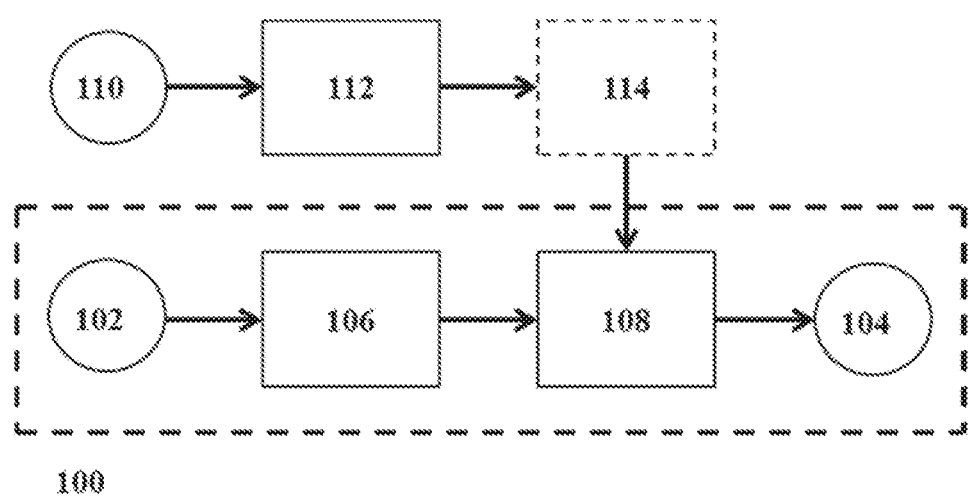
FIG. 1 provides a schematic illustration of the products of an oxidative coupling of methane (OCM) process being integrated with a hydrocarbons process.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "$C_{2+}$," as used herein, generally refers to a compound comprising two or more carbon atoms. $C_{2+}$ compounds include, without limitation, alkanes, alkene, alkynes, aldehyes, ketones, aromatics esters and carboxylic acids containing two or more carbon atoms. Examples of $C_{2+}$ compounds include ethane, ethene, ethyne, propane, propene and propyne.

The term "non-$C_{2+}$ impurities," as used herein, generally refers to material that does not include $C_{2+}$ compounds. Examples of non-$C_{2+}$ impurities include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "natural gas processing facility," as used herein, generally refers to a facility that takes in one or more of natural gas or NGLs, and produces more than one product from these inputs.

The term "methane conversion," as used herein, generally refers to the percentage or fraction of methane introduced into the reaction that is converted to a product other than methane.

The term "$C_{2+}$ selectivity," as used herein, generally refers to the percentage of all carbon containing products of an oxidative coupling of methane (OCM) reaction that are the desired or otherwise preferable $C_{2+}$ products, e.g., ethane, ethylene, propane, propylene, etc. Although primarily stated as $C_{2+}$ selectivity, it will be appreciated that selectivity may be stated in terms of any of the desired products, e.g., just $C_2$, or just $C_2$ and $C_3$.

The term "$C_{2+}$ yield," as used herein, generally refers to the amount of carbon that is incorporated into a $C_{2+}$ product as a percentage of the amount of carbon introduced into a reactor in the form of methane. This may generally be calculated as the product of the conversion and the selectivity divided by the number of carbon atoms in the desired product. $C_{2+}$ yield is typically additive of the yield of the different $C_{2+}$ components included in the $C_{2+}$ components identified, e.g., ethane yield+ethylene yield+propane yield+ propylene yield etc.).

The term "OCM process," as used herein, generally refers to a process that employs or substantially employs an oxidative coupling of methane (OCM) reaction.

The term "non-OCM process," as used herein, generally refers to a process that does not employ or substantially employ an oxidative coupling of methane reaction. Examples of processes that may be non-OCM processes include non-OCM hydrocarbon processes, such as, for example, an oil refinery, a natural gas liquids process, or a cracker.

The term "substantially equivalent," as used herein in the context of methane concentration, generally means that the methane concentration is within approximately 80%, 70%, 60%, 50%, 40%, 30%, 20%, 10%, or 5% of the methane concentration typically passed into a existing fractionation train of a gas facility or cracker facility.

Integration of OCM with Hydrocarbon Processes

The present disclosure provides for the integration of oxidative coupling of methane ("OCM") and optionally or additionally, oxidative dehydrogenation of ethane to ethylene or propane to propylene ("ODH") processes and systems into existing natural gas and other petrochemical processes and facilities in order to gain advantages of feedstock flexibility, energy efficiency, and flexibility to better define the resulting product slates from those processes. In particular, by providing an integrated OCM process with other processes, one can take advantage of the complementarity of the OCM processes with these other gas or petrochemical processes to improve one or all of feedstock flexibility, product slate flexibility, energy efficiency, and other advantaged process parameters. While this integration provides benefits to a number of different processes and systems, for ease of illustration, it is described in greater detail with respect to integration into existing hydrocarbon processes (e.g., natural gas NGL processes, olefin production processes from ethane, ethane/propane, and/or naphtha, as well as petroleum refining).

An OCM process can take as input methane and generate as product (or output) one or more hydrocarbons, such as $C_{2+}$ compounds, as well as the heat from the exothermic reaction. The OCM process can be facilitated by a catalyst. An example OCM process is as follows: $2CH_4+O_2 \rightarrow C_2H_4+2H_2O$.

Reference will now be made to the figures, wherein like numerals refer to like parts throughout. it will be appreciated that the figures and features therein are not necessarily drawn to scale.

The methane ($CH_4$) input can be provided from various sources, and the product(s) from the OCM process can be directed into various downstream processes. An OCM process can be integrated with the hydrocarbon process in any number of ways. FIG. 1 shows an example of integrating an OCM process with a hydrocarbons process 100. The hydrocarbon process can take any feedstock 102 and convert it to one or more products 104 using any number of operations (e.g., 106 and 108), such as refinery, NGL fractionation, ethane cracking or other hydrocarbon process operations. In some cases, in the OCM processes, methane (e.g., from a geological, biological source, or industrial hydrocarbon source) 110 is fed into an OCM process 112 (e.g., an OCM reactor) to produce $C_{2+}$ compounds. The $C_{2+}$ compounds can be integrated with a hydrocarbons process. In some cases, the $C_{2+}$ compounds can be enriched and/or purified in a separations module 114, for example, to at least approximately match the composition of a stream in the hydrocarbons process having $C_{2+}$ compounds 108.

Figure 2:
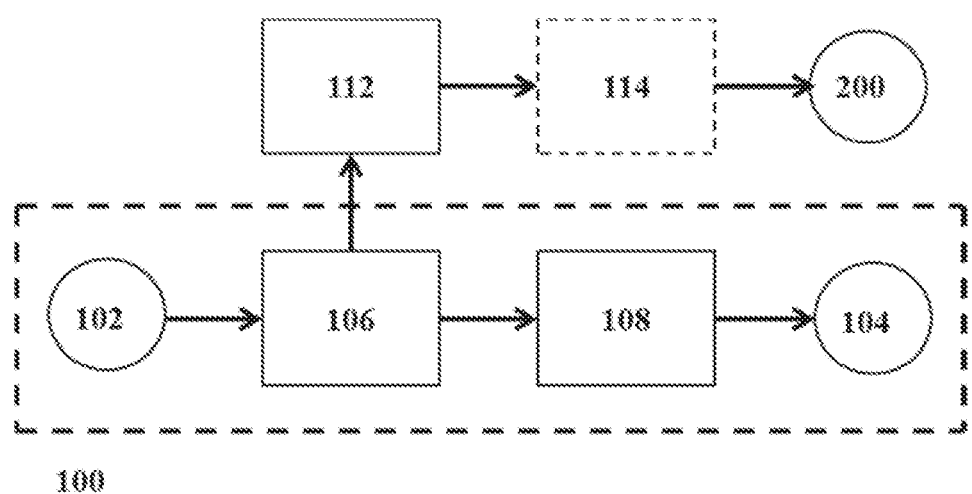
FIG. 2 provides a schematic illustration of methane for an OCM process being provided by a hydrocarbons process.

FIG. 2 shows another example of integration with a hydrocarbons process. In this case, methane is provided from a stream of the hydrocarbon process having methane 106. The methane can be converted to $C_{2+}$ compounds in process 112 and, in some cases, separated in process 114 to provide a product stream having the $C_{2+}$ compounds 200.

Figure 3:
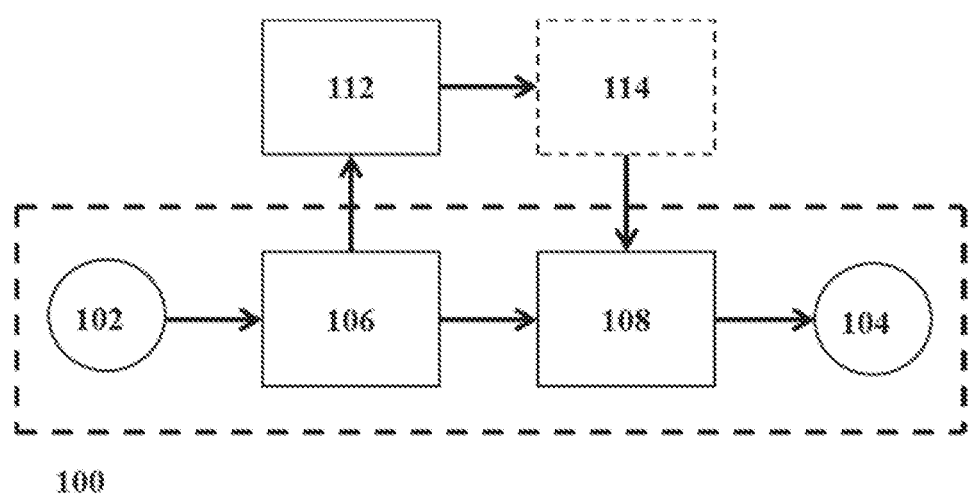
FIG. 3 provides a schematic illustration of methane for an OCM process being provided by a hydrocarbons process and the products of an OCM process being integrated with the hydrocarbons process.

Yet another example is shown in FIG. 3. Here, methane is provided from a stream of the hydrocarbon process having methane 106, converted to $C_{2+}$ compounds in process 112, optionally separated in process 114, and integrated with a stream of the hydrocarbons process 108 having $C_{2+}$ compounds.

Figure 4:
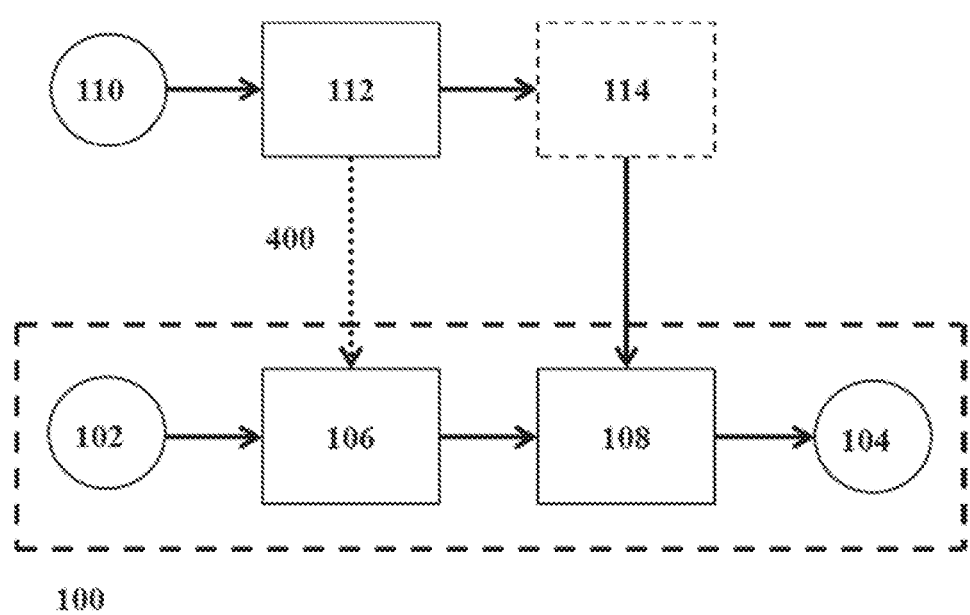
FIG. 4 provides a schematic illustration of heat from an OCM process being integrated with a hydrocarbons process.

An OCM processes can be an exothermic processes, yielding heat that can be employed for use in various processes. In some cases, the OCM process is integrated with respect to energy, in some instances in addition to integration of material streams. FIG. 4 shows an example where heat 400 is transferred from an OCM reactor 112 to a portion of the hydrocarbon process requiring heat 106. In some cases, methane is also withdrawn from the hydrocarbons process and/or $C_{2+}$ compounds are fed into the hydrocarbons process. The withdrawn or excess methane can be combusted to provide energy to the hydrocarbons process.

Provided herein are various types of hydrocarbon processes that can be integrated with an OCM process and examples of separations (e.g., rough cut separations) that can be performed.

Integrated Catalytic Systems

In some embodiments, existing gas or petrochemical processing facilities or systems are integrated with novel processes and systems to yield a synergistic and highly valuable overall process. In some cases, additional value-add catalytic reaction processes and reactor systems are integrated into conventional natural gas or other petrochemical processing facilities and systems to take in one or more outputs of these facilities and systems and/or provide one or more inputs into these facilities and systems, to leverage efficiency advantages derived from the combination of these processes over and above those processes individually. In some instances, these integrated catalytic reactor systems will typically (1) take in one or more final or intermediate product streams from the processes performed in these facilities to catalytically convert those final or intermediate product streams into higher value or more easily managed materials, (2) contribute one or more of final or intermediate product streams to be further processed within one or more different processing units within these facilities, and/or (3) contribute and/or utilize thermal energy required by or produced by these processing systems.

The resulting integrated processing facilities can have greatly enhanced efficiency and profitability, both in terms of the products produced as a function of the raw materials consumed, the types of feedstocks used, the types of products produced, and in terms of the energy requirements for operating those facilities. Consequently, the environmental impact of these facilities can be substantially reduced, both in terms of reduced waste and reduced consumption of externally generated energy.

In some cases, integrated reactor systems for carrying out exothermic catalytic reactions can be used to convert natural gas constituents to higher value components, such as for converting methane and ethane to higher alkanes, olefins, and the like. Examples of such reactions include exothermic catalytic reactions for, e.g., the oxidative coupling of methane (OCM), as well as the oxidative dehydrogenation (ODH) of, e.g., ethane, propane and other hydrocarbons.

The oxidative coupling of methane ("OCM") to ethylene can involve the following reaction: $2CH_4+O_2 \rightarrow C_2H_4+2H_2O$ (See, e.g., Zhang, Q., *Journal of Natural Gas Chem.*, 12:81, 2003; Olah, G. "Hydrocarbon Chemistry", Ed. 2, John Wiley & Sons (2003)). This reaction is exothermic ($\Delta H=-67$ kcals/mole) and has typically been shown to occur at very high temperatures (>700° C.). Although the detailed reaction mechanism may not be fully characterized, and without being bound by theory, experimental evidence suggests that free radical chemistry may be involved (Lunsford, *J. Chem. Soc., Chem. Comm.*, 1991; H. Lunsford, *Angew. Chem., Int. Ed. Engl.*, 34:970, 1995). In the reaction, methane ($CH_4$) can activated on the catalyst surface, forming methyl radicals which then couple in the gas phase to form ethane ($C_2H_6$), followed by dehydrogenation to ethylene ($C_2H_4$). Several catalysts have shown activity for OCM, including various forms of iron oxide and oxides of vanadium, molybdenum, cobalt, platinum, rhodium, lithium, zirconium, gold, silver, manganese, cerium, magnesium, lanthanum, sodium, zinc and combinations thereof (e.g, $V_2O_5$, $MoO_3$, $Co_3O_4$, Pt—Rh, $Li/ZrO_2$, Ag—Au, $Au/Co_3O_4$, Co/Mn, $CeO_2$, MgO, $La_2O_3$, $Mn_3O_4$, $Na_2WO_4$, MnO, ZnO), on various supports. A number of doping elements can also be useful in combination with the above catalysts.

Since the OCM reaction was first reported over thirty years ago, it has been the target of intense scientific and commercial interest. In some cases, the fundamental limitations of the conventional approach to C—H bond activation appear to limit the yield of this attractive reaction under practical operating conditions. Specifically, numerous publications from industrial and academic labs have consistently demonstrated characteristic performance of high selectivity at low conversion of methane, or low selectivity at high conversion (J. A. Labinger, *Cat. Lett.*, 1:371, 1988). Limited by this conversion/selectivity threshold, some OCM catalysts do not exceed 20-25% combined $C_2$ yield (i.e. ethane and ethylene). In some cases, such high conversions and selectivities are at extremely high temperatures (>800 C), low pressures, and low gas hourly space velocity. Novel catalysts and systems have been developed, however, that can operate within lower temperature environments with higher yield/selectivity (See, e.g., U.S. Published U.S. Patent Application Nos. 2012/0041246, and 2013/0023709.

Although primarily described in terms of integrating an OCM reactor system, additional reactor systems may likewise be integrated, such as ODH reactor systems. In some cases, oxidative dehydrogenation (ODH) of light alkanes offers an attractive route to alkenes, since, like the OCM reaction, the reaction is exothermic and avoids the thermodynamic constraints of non-oxidative routes by forming water as a byproduct. In addition, carbon deposition during ODH can be dramatically reduced, leading to stable catalytic activity. However, the yield of alkenes obtained by ODH can be limited on most catalysts by alkene combustion to CO and $CO_2$ (e.g., of $CO_x$).

In an aspect, the present disclosure provides modular OCM reactor systems that can be configured to "plug in" to, and in some aspects are integrated into existing natural gas processing facilities. As such, a gas processing plant can take in natural gas and produce pipeline ready natural gas as well as NGLs, or it can take in NGLs and fractionate them to produce two or more different NGL products therefrom. In some cases, the specific configuration and type of processing plant will depend upon the material taken in and the products produced therefrom, and can encompass in many cases, for example, NGL extraction plants, fractionators, straddle plants, and the like, that meet the aforementioned criteria.

In some aspects, the processing facilities include one or more of an extraction unit and a fractionation unit, and optionally one or more additional processing units (e.g., without extensive customized retrofitting to such facilities). Further, the integrated OCM reactor systems can be integrated and configured to take up one or more effluent streams from different processing units within these facilities as a feed stream to the OCM reactor system, contribute one or more effluent streams to one or more different processing units within these facilities as a feed stream to those units, utilize thermal energy produced elsewhere in the facility to carry out the OCM reaction, and/or contribute thermal energy to other systems and processing units elsewhere in the facility.

As used herein, an OCM reactor system typically includes one or more reactor vessels that contain an appropriate OCM catalyst material, typically in conjunction with additional system components. A variety of OCM catalysts have been described previously, such as, e.g., in U.S. Pat. Nos. 5,712,217; 6,403,523 and 6,576,803, which are entirely incorporated herein by reference. While these catalysts have been shown to catalyze an OCM reaction, for most of these catalysts, the reactions are carried out under conditions that are less practical or economical, i.e., at very high temperatures and/or pressures (e.g., greater than 800° C.). Some catalysts yield conversion and selectivity that allow for economic methane conversion at practical operating conditions. Examples of such catalysts are described in, for example, U.S. Patent Publication No. 2012/0041246 and U.S. Patent Publication No. 2013/0023709, which are entirely incorporated herein by reference.

Products produced from these catalytic reactions typically include CO, $CO_2$, $H_2$, $H_2O$, $C_2+$ hydrocarbons, such as ethylene, ethane, and larger alkanes and alkenes. In some embodiments, the OCM reactor systems operate to convert methane, e.g., the methane component of natural gas, into desired higher hydrocarbon products (ethane, ethylene, propane, propylene, butanes, pentanes, etc.) collectively referred to as $C_2+$ compounds with high yield. In particular, the progress of the OCM reaction is generally discussed in terms of methane conversion, $C_2+$ selectivity, and $C_2+$ yield.

In some cases, OCM reactor systems typically provide a methane conversion of at least 10% per process pass in a single integrated reactor system (e.g., single isothermal reactor system or integrated multistage adiabatic reactor system), with a $C_2+$ selectivity of at least 50%, at reactor inlet temperatures of between 400 and 600° C. and at reactor inlet pressures of between about 15 pounds per square inch gauge (psig) and about 150 psig. In some cases, the single pass conversion is 10% or greater with a selectivity of 60% or greater, and in some cases, a conversion of 15% or greater, with a selectivity of 50% or greater, or even a selectivity of 60% or greater. Likewise, in some cases, the reactor inlet pressures are between about 15 and about 135 psig, in some cases, less than about 120 psig, less than about 100 psig, less than about 90 psig, less than about 85 psig, or less than about 80 psig, or even less than about 70 psig. In some cases, the reactor inlet pressure is between about 30 and about 100 psig, or even between about 30 psig and one of about 90, or 85, or 80 psig, (e.g., while achieving the selectivities and conversions, described above). In some cases, the catalysts employed within these reactor systems are capable of providing the described conversion and selectivity under the described reactor conditions of temperature and pressure. In some cases, the reactor inlet or feed temperatures typically substantially correspond to the minimum "light-off" or reaction initiation for the catalyst or system. In other words, the feed gases can be contacted with the catalyst at a temperature at which the OCM reaction is able to be initiated upon introduction to the reactor. Because the OCM reaction is exothermic, once light-off is achieved, the heat of the reaction can be expected to maintain the reaction at suitable catalytic temperatures, and even generate excess heat.

In some embodiments, the OCM reactors and reactor systems, when carrying out the OCM reaction, operate at pressures of between about 15 psig and about 125 psig at the above described temperatures, while providing the conversion and selectivity described above, and in some cases, at pressures less than 100 psig (e.g., between about 15 psig and about 100 psig, or even less than about 90 psig).

Examples of catalyst materials are described in, for example, U.S. Patent Publication No. 2012/0041246 and U.S. Patent Publication No. 2013/0023709, which are entirely incorporated herein by reference. The catalysts can comprise bulk catalyst materials, e.g., having relatively undefined morphology or, in some cases, the catalyst material comprises, at least in part, nanowire containing catalytic materials. In any form, the catalysts used in accordance with the present disclosure can be specifically employed under the full range of reaction conditions described above, or in any narrower described range of conditions. Similarly, the catalyst materials can be provided in a range of different larger scale forms and formulations, e.g., as mixtures of materials having different catalytic activities, mixtures of catalysts and relatively inert or diluent materials, incorporated into extrudates, pellets, or monolithic forms, or the like. Ranges of exemplary catalyst forms and formulations are described in, for example, U.S. patent application Ser. No. 13/901,319, filed May 23, 2013, the full disclosure of which is incorporated herein by reference in its entirety for all purposes.

The reactor vessels used for carrying out the OCM reaction in the OCM reactor systems of the invention can include one or more discrete reactor vessels each containing OCM catalyst material, fluidly coupled to a methane source and a source of oxidant as further discussed elsewhere herein. Feed gas containing methane can be contacted with the catalyst material under conditions suitable for initiation and progression of the reaction within the reactor to catalyze the conversion of methane to ethylene and other products.

For example, the OCM reactor system can comprise one or more staged reactor vessels operating under isothermal or adiabatic conditions, for carrying out OCM reactions. For adiabatic reactor systems, the reactor systems can include one, two, three, four, five or more staged reactor vessels arranged in series, which are fluidly connected such that the effluent or "product gas" of one reactor is directed, at least in part, to the inlet of a subsequent reactor. Such staged serial reactors can provide higher yield for the overall process, by allowing catalytic conversion of previously un-reacted methane. These adiabatic reactors are generally characterized by the lack of an integrated thermal control system used to maintain little or no temperature gradient across the reactor. Without integrated temperature control system, the exothermic nature of the OCM reaction can result in a temperature gradient across the reactor indicative of the progress of the reaction, where the inlet temperature can range from about 400° C. to about 600° C., while the outlet temperature ranges from about 700° C. to about 900° C. Typically, such temperature gradients can range from about 100° C. to about 500° C. In some cases, the adiabatic reactors are staged, with inter-stage cooling systems to step through a more complete catalytic reaction without generating extreme temperatures, e.g., in excess of 900° C.

In operation, methane-containing feed gas can be introduced into the inlet side of a reactor vessel, e.g., the first reactor in a staged reactor system. Within this reactor, the methane can be converted into $C_2+$ hydrocarbons, as well as other products, as discussed above. At least a portion of the product gas stream can then be cooled to an appropriate temperature and introduced into a subsequent reactor stage for continuation of the catalytic reaction. In some cases, the effluent from a preceding reactor, which in some cases may include un-reacted methane, can provide at least a portion of the methane source for a subsequent reactor. An oxidant source and a methane source, separate from the un-reacted methane from the first reactor stage, can also typically be coupled to the inlet of each subsequent reactor.

In some cases, the reactor systems can include one or more 'isothermal' reactors, that maintain a relatively low temperature gradient across the length or depth of the overall reactor bed, e.g., between the inlet gas and outlet or product gas, through the inclusion of integrated temperature control elements, such as coolant systems that contact heat exchange surfaces on the reactor to remove excess heat, and maintain a flat or insignificant temperature gradient between the inlet and outlet of the reactor. Typically, such reactors utilize molten salt or other coolant systems that operate at temperatures below 593° C. As with adiabatic systems, isothermal reactor systems can include one, two, three, ten or more reactors that may be configured in serial or parallel orientation. Reactor systems for carrying out these catalytic reactions are also described in U.S. patent application Ser. No. 13/900,898, filed May 23, 2013, the full disclosure of which is incorporated herein by reference in its entirety for all purposes.

The OCM reactor systems also typically include thermal control systems that are configured to maintain a desired thermal or temperature profile across the overall reactor system, or individual reactor vessels. In the context of adiabatic rector systems, the thermal control systems can include, for example, heat exchangers disposed upstream, downstream or between serial reactors within the overall system in order to maintain the desired temperature profile across the one or more reactors. In the context of reactors carrying out exothermic reactions, like OCM, such thermal control systems also optionally include control systems for modulating flow of reactants, e.g., methane containing feed gases and oxidant, into the reactor vessels in response to temperature information feedback, in order to modulate the reactions to achieve the thermal profiles of the reactors within the desired temperature ranges. These systems are also described in U.S. patent application Ser. No. 13/900, 898, previously incorporated herein by reference.

For isothermal reactors, such thermal control systems can include the foregoing, as well as integrated heat exchange components, such as integrated heat exchangers built into the reactors, such as tube/shell reactor/heat exchangers, where a void space is provided surrounding a reactor vessel or through which one or more reactor vessels or tubes pass. A heat exchange medium can then be passed through the void to remove heat from the individual reactor tubes. The heat exchange medium can then be routed to an external heat exchanger to cool the medium prior to recirculation into the reactor.

In some cases, the products of the OCM reactor systems integrated into processing facilities are transferred to additional process components for production of higher hydrocarbons, e.g., $C_3+$ hydrocarbons from the products of the OCM reaction. In particular, $C_2+$ hydrocarbons derived from the OCM reaction process, and which optionally include the extraction processes described above or are upstream of such extraction processes, are subjected to additional processing for conversion of the $C_2+$ hydrocarbons, like ethylene, into even higher hydrocarbons, like $C_3+$ hydrocarbons, NGLs, cyclic hydrocarbons, or linear and branched alkanes, aromatics. In some cases, although generally phrased in terms of the effluent from the OCM reactor system, effluent from individual reactor stages can be routed to follow on process steps, including, e.g., de-methanization, where separated $C_2+$ compounds are routed to a different process, while the methane rich streams are passed through subsequent reactor stages. As a result, efficiencies in processing and reaction equilibria can be favorably controlled over multiple stages.

For ease of discussion, these additional processes are generally referred to herein as "oligomerization" processes, although this term encompasses a range of different reaction types. Likewise, the processing units or systems for carrying out these reactions are generally referred to herein as "oligomerization systems" or "units", although such terminology includes a range of different reactions for conversion of higher hydrocarbons from $C_2$ hydrocarbons, e.g., ethane and ethylene. Examples of such reactions include, for example; targeted oligomerization of ethylene optionally followed by hydrogenation to form narrow distributions of linear or branched alkanes such as butanes, hexanes, octanes, decanes, dodecanes, tetradecanes, etc, non-targeted oligomerization of ethylene optionally followed by hydrogenation to form broad distributions of linear or branched alkanes such as hydrocarbons within the $C_4$-$C_{16}+$ range, dimerization of ethylene to butenes followed by dimerization to i-octanes, non-targeted oligomerization of ethylene optionally followed by hydrogenation to form a mixture of aromatics, alkanes, alkenes, that is nominally a gasoline blendstock, non-targeted oligomerization of ethylene optionally followed by hydrogenation to form a mixture of branched, non-branched, and cyclic alkanes that is nominally a diesel or jet fuel blendstock, non-targeted oligomerization of ethylene to form narrow distributions of aromatics, such as benzene, toluene and xylenes (collectively, "BTX"), or benzene, toluene, ethyl-benzene, xylene ("BTEX"), for use as a chemical feedstock. In general, many of these oligomerization processes involve catalytic reactions and reactor systems for conversion of $C_2+$ hydrocarbons to larger hydrocarbons. The nature and configuration of the oligomerization reactor and catalyst system can depend upon the specific type of product desired. In some embodiments, the oligomerization reaction takes place over a heterogeneous catalyst in a fixed bed reactor (either adiabatic or isothermal) although methods and processes for homogeneous catalysts are suitable, and these can be used in combination such as a heterogeneous process for dimerization of ethylene to butenes and homogeneous process for butenes to octenes. A variety of these further conversion processes that can be integrated into the processes described herein, are described in, e.g., U.S. Provisional Patent Application No. 61/734,865, filed Dec. 7, 2012, the full disclosure of which is hereby incorporated herein by reference in its entirety for all purposes.

In some cases, the outputs of the additional processes, e.g., oligomerization processes, can be routed through the integrated unit operations of a gas processing facility, cracker facility or other processing facility. For example, separation processes can be equally applicable to the oligomerization products as they are to OCM products and cracking products. Further, oligomerization products may be routed into upstream unit processes, including the cracker itself, for back-cracking of LAOs or other higher hydrocarbons to form more diverse products.

For ease of discussion, in addition to one or more reactor vessels and associated piping and conduits, the phrase "OCM reactor system" also typically includes those elements that allow ready integration of an OCM process into an existing gas processing path or plant. As such, such OCM reactor systems can include heat exchangers for both elevating the temperature of feed gases to reach appropriate temperatures for catalysis, as well as cool product gases to meet temperature requirements of subsequent process steps. Similarly, such reactor systems can include compressors, pumps and the like, for applying appropriate pressures for delivering feed gases or recycle streams into the reactor systems and/or product streams to other processing units, e.g., separation or fractionation units.

Separations

The higher hydrocarbons ($C_{2+}$) produced in an OCM reactor can be integrated with (e.g., fed into) a hydrocarbon process as described herein. In some cases, integration with the hydrocarbon process can use separations equipment from the hydrocarbons process, thereby eliminating or reducing the amount of separations equipment that is needed to add an OCM component to an existing hydrocarbons process. Nonetheless, in some cases, separations are performed on the OCM product stream prior to feeding into the hydrocarbon process. The separations can achieve any number of objectives, including but not limited to matching the composition of the OCM product stream to the stream of the hydrocarbons process to which it is being integrated and/or reducing the volume of the stream (e.g., by partially enriching the $C_{2+}$). Also provided herein are the processes and systems for performing the described methods.

Some separations processes for recovering $C_{2+}$ compounds from OCM product streams include the use of cryogenic separations as described in U.S. patent application Ser. No. 13/739,954 ("PROCESS FOR SEPARATING HYDROCARBON COMPOUNDS"), which is incorporated herein by reference in its entirety for all purposes. However, cryogenic separations can be expensive due to high energy demands so the present disclosure provides methods for performing an initial "rough cut" separation to remove impurities and inert compounds, thereby concentrating the $C_2+$ stream and effectively reducing the amount of gas entering the cryogenic separation unit per unit of desired product, thereby reducing the cost of cryogenic separation. Such a rough cut separation can be beneficial when the source of oxygen for the OCM reaction is air.

The separations can be performed in a separations module comprising any number of individual pieces of equipment (unit operations) working together to achieve a separation. In some cases, the separations module has 1, 2, 3, 4, 5, 6, 7, 8, 9, 10, 11, 12, 13, 14, 15, 16, 17, 18, 19, 20, or more pieces of equipment. The separations units can be disposed in series, parallel, or both (e.g., some situated in series and others situated in parallel).

In an aspect, a method for recovering hydrocarbons having two or more carbon atoms ($C_{2+}$) from an oxidative coupling of methane (OCM) comprises providing an OCM product stream comprising $C_{2+}$ hydrocarbons, impurities, and un-reacted methane. In some cases, the OCM product stream is provided by performing an OCM reaction. Any suitable amount of the methane can be converted into $C_{2+}$ hydrocarbons (e.g., at least 1%, at least 3%, at least 5%, at least 10%, or at least 20%).

The method can then include performing a separation that provides a first stream comprising the impurities and/or inert components, provides a second stream enriched in methane, and provides a third stream enriched in $C_{2+}$ hydrocarbons. The three streams can be provided by performing a separation. In some cases, the separation includes pressure swing adsorption. The method can include temperature swing adsorption (TSA), cooling, pressurizing, and/or vacuum pumping the third stream to condense the $C_{2+}$ hydrocarbons. In an example, the method includes TSA, cooling, pressurizing, vacuum pumping, and then cooling the third stream to condense the $C_{2+}$ hydrocarbons.

In some cases, the second stream is flowed into an OCM reactor, thereby recycling the un-reacted methane. In some cases, the second stream is flared or used as fuel in a hydrocarbons process. As described herein, the heat generated by the OCM reactor can be integrated with any suitable portion of the hydrocarbons process. In some cases, the third stream (comprising $C_{2+}$ hydrocarbons) is flowed into a hydrocarbons process.

The first stream can include any suitably large proportion of the impurities and/or inert components (i.e., reducing the amount of material going into a cryogenic separations unit). In some cases, about 60%, about 70%, about 80%, about 90%, or about 95% of the impurities and/or inert components that exit the OCM reactor are separated into the first stream. In some instances, at least about 60%, at least about 70%, at least about 80%, at least about 90%, or at least about 95% of the impurities and/or inert components that exit the OCM reactor are separated into the first stream. In some cases, the impurities and/or inert components are derived from air. The impurities and/or inert components can be any compound, but in some cases comprise argon (Ar), hydrogen ($H_2$), carbon monoxide (CO), carbon dioxide ($CO_2$), water ($H_2O$), nitrogen ($N_2$), or any combination thereof.

The rough cut separation described herein can reduce the volumetric flow rate of the third stream compared with the volumetric flow rate of the OCM product stream. In some embodiments, the volumetric flow rate of the third stream is about 5%, about 10%, about 15%, about 20%, about 30%, about 35%, about 40%, about 45%, or about 50% of the volumetric flow rate of the OCM product stream at a constant temperature and pressure. In some cases, the volumetric flow rate of the third stream is at most about 5%, at most about 10%, at most about 15%, at most about 20%, at most about 30%, at most about 35%, at most about 40%, at most about 45%, or at most about 50% of the volumetric flow rate of the OCM product stream at a constant temperature and pressure.

Figure 5:
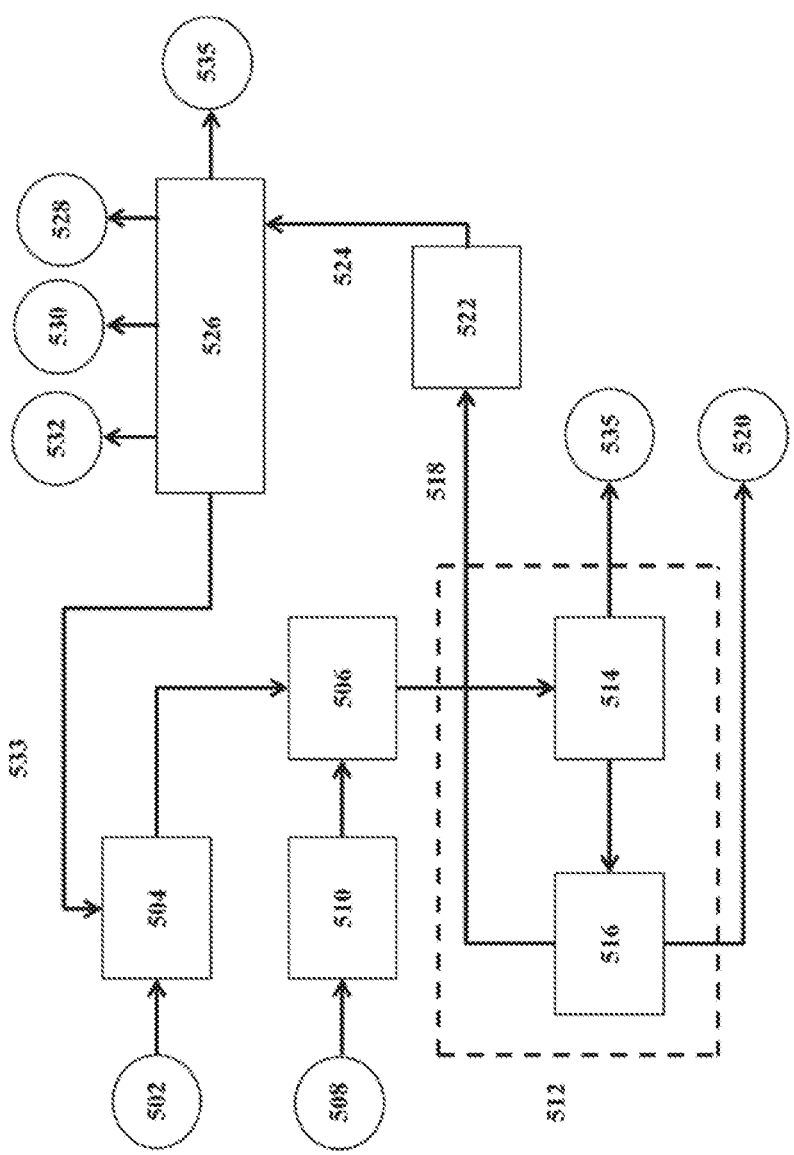
FIG. 5 provides a schematic illustration of an OCM process having a separations module comprising a dryer and a nitrogen recovery unit.

FIG. 5 provides an example of a process for performing separations (e.g., prior to integrating with a hydrocarbon process. In some cases, methane (e.g., natural gas) 502 is heated 504 and injected into an OCM reactor 506. A source of oxygen (e.g., air) 508 can also be heated 510 and injected into the OCM reactor. In some cases, the natural gas and the air are heated in the same heater.

In some cases, the products produced in the OCM reactor (e.g., $C_{2+}$ hydrocarbons) are separated from the OCM reactor effluent via chemical absorption. An example of chemical absorption can be achieved by contacting the gaseous reactor mixture effluent with an aqueous or organic solution containing metallic ions (such as copper and silver) able to bind with the olefins contained in the reactor effluent. The olefins contained in the solution can then be stripped in a suitably designed unit operation (for example, a packed or trayed column) via pressure reduction and/or temperature increase.

The products produced in the OCM reactor (e.g., $C_{2+}$ hydrocarbons) as well as impurities, inert components (e.g., argon, nitrogen, water) and un-reacted methane can be fed into a separations module comprising one or more unit operations as depicted in the dotted border 512. In some instances, the separations module reduces the downstream compression of the third stream by about 40%, about 50%, about 60%, about 70%, about 80%, or about 90% when compared with cryogenic separation. In some embodiments, the separation module reduces the downstream compression of the third stream by at least about 40%, at least about 50%, at least about 60%, at least about 70%, at least about 80%, at least about 90%, at least about 95%. The separation module can eliminate the amine units and/or cryogenic separation units. The cryogenic separations unit can be replaced with a smaller refrigeration unit in some instances.

In some cases, the separations module comprises a dryer 514 and a nitrogen recovery unit 516. As shown here, the products from the OCM reactor can be initially fed into a dryer 514 where water 535 is removed. Any suitable amount of water can be removed, including at least 80%, at least 90%, at least 95%, at least 99%, or at least 99.9%.

Following the dryer 514, the remaining components can be fed into a nitrogen recovery unit (NRU) 516. The NRU can be any type of unit operation. In some cases, the NRU is a pressure swing adsorption unit (PSA). The NRU generally separates hydrocarbons 518 (e.g., methane and higher hydrocarbons) from other gases such as impurities and inert components 520. The impurities and inert components include, but are not limited to argon (Ar), hydrogen ($H_2$), carbon monoxide (CO), carbon dioxide ($CO_2$), and nitrogen ($N_2$). In some cases, the impurities and inert components include some un-reacted methane ($CH_4$). The NRU 516 generally removes the majority of the impurities and inert components 520, however some of the impurities and inert components can be removed at other portions of the process (e.g., at stream 535). In some cases, the NRU removes about 60%, about 70%, about 80%, about 90%, about 95%, about 97%, about 99%, or about 99.5% of the impurities and inert components (e.g., when comparing the mass flow rate of stream 520 with stream 535). In some embodiments, the NRU removes at least about 60%, at least about 70%, at least about 80%, at least about 90%, at least about 95%, at least about 97%, at least about 99%, or at least about 99.5% of the impurities and inert components.

The hydrocarbon stream 518 from the NRU 516 can be fed into one or more compressors 522. The compressors are generally smaller and/or require less energy than would be required in the absence of the separations module 512 (i.e., because the majority of the impurities and inert components). In some cases, the compressors are about 10%, about 20%, about 30%, about 40%, about 50%, about 60%, about 70%, or about 80% of the size as would be required in the absence of the separations module. In some cases, the compressors are less than about 10%, less than about 20%, less than about 30%, less than about 40%, less than about 50%, less than about 60%, less than about 70%, or less than about 80% of the size as would be required in the absence of the separations module. In some instances, the compressors are between about 10% and 60% of the size as would be required in the absence of the separations module. In some cases, the compressors require about 10%, about 20%, about 30%, about 40%, about 50%, about 60%, about 70%, or about 80% of the energy as would be required in the absence of the separations module. In some cases, the compressors require less than about 10%, less than about 20%, less than about 30%, less than about 40%, less than about 50%, less than about 60%, less than about 70%, or less than about 80% of the energy as would be required in the absence of the separations module.

The compressed hydrocarbon stream 524 can be fed into a refrigeration unit 526. The refrigeration unit can decrease the temperature of the compressed hydrocarbons such that one or more hydrocarbons are condensed. In some cases, the temperature is lowered in stages such that a series of various hydrocarbons are condensed according to their boiling points. For example, hydrocarbons having three or more carbons can be condensed first 528 (e.g., at a temperature of less than −42° C.). The temperature can be lowered further such that ethane ($C_2H_6$) is condensed 530. In some cases, the temperature is lowered (in one or more stages) such that ethylene ($C_2H_4$) condenses 532 (e.g., at less than −103° C.).

In some cases, un-reacted methane 533 is returned to the OCM reactor 506, either directly or through a heater 504. Impurities and inert components can be removed from any portion of the process, including from the refrigeration unit 535.

The refrigeration unit(s) is generally smaller and/or require less energy than would be required in the absence of the separations module 512 (i.e., because the majority of the impurities and inert components). In some cases, the refrigeration unit is about 10%, about 20%, about 30%, about 40%, about 50%, about 60%, about 70%, or about 80% of the size as would be required in the absence of the separations module. In some cases, the refrigeration unit is less than about 10%, less than about 20%, less than about 30%, less than about 40%, less than about 50%, less than about 60%, less than about 70%, or less than about 80% of the size as would be required in the absence of the separations module. In some instances, the refrigeration unit is between about 10% and 60% of the size as would be required in the absence of the separations module. In some cases, the refrigeration unit requires about 10%, about 20%, about 30%, about 40%, about 50%, about 60%, about 70%, or about 80% of the energy as would be required in the absence of the separations module. In some cases, the refrigeration unit requires less than about 10%, less than about 20%, less than about 30%, less than about 40%, less than about 50%, less than about 60%, less than about 70%, or less than about 80% of the energy as would be required in the absence of the separations module.

Addition of a $C_{2+}$ bed (e.g., separation or concentration bed) to the separations module 512 shown in FIG. 5 can reduce the size and/or energy required in a refrigeration and/or cryogenic separation unit. The $C_{2+}$ bed can be any unit that increases the concentration of $C_{2+}$ compounds (e.g., a pressure swing adsorption unit (PSA), a temperature swing adsorption unit (TSA), a membrane separator, a lean oil adsorption unit, silver (Ag) adsorption unit, and the like). The present disclosure provides the use of pressure swing adsorption (PSA) to concentrate hydrocarbons having greater than or equal to two carbon atoms ($C_{2+}$), in some case between two and five carbons ($C_{2-5}$).

In an aspect, a method for concentrating hydrocarbons having between two and five carbons ($C_{2-5}$) comprises introducing a fluid (e.g., OCM product stream) comprising $C_{2+}$ compounds, in some cases $C_{2-5}$ compounds, into a vessel at a first pressure. The vessel can contain an adsorbent medium.

The adsorbent medium can be any medium suitable for performing PSA. In some cases, the medium is a molecular sieve. The medium can be a micro-porous material which can selectively adsorb gases and/or liquid. In some cases, they are synthetic zeolites such as crystalline metal aluminosilicates. The medium can have any suitable pore size including about 1 angstrom, about 2 angstroms, about 3 angstroms, about 4 angstroms, about 5 angstroms, about 6 angstroms, about 7 angstroms, about 8 angstroms, about 9 angstroms, or about 10 angstroms. In some cases, medium has a pore size of at most about 1 angstrom, at most about 2 angstroms, at most about 3 angstroms, at most about 4 angstroms, at most about 5 angstroms, at most about 6 angstroms, at most about 7 angstroms, at most about 8 angstroms, at most about 9 angstroms, or at most about 10 angstroms. In some cases, medium has a pore size of at least about 1 angstrom, at least about 2 angstroms, at least about 3 angstroms, at least about 4 angstroms, at least about 5 angstroms, at least about 6 angstroms, at least about 7 angstroms, at least about 8 angstroms, at least about 9 angstroms, or at least about 10 angstroms.

In other cases, the adsorbent can be suitably designed to chemically bind with selected components of the reactor effluent. For example, the adsorbent may contain specific metals (such as copper or silver) that can bind with the olefins in the reactor effluent.

Next, the pressure in the vessel is changed to a second pressure. The first pressure can be higher than the second pressure or the second pressure can be higher than the first pressure. The method can also include cycling through two or more pressures, or changing the pressure in any suitable manner such that $C_{2+}$ compounds (e.g., $C_{2-5}$) are separated. In an example, the pressure can be increased with the aid of a compressor. In an example, the pressure can be decreased with the aid of a pump.

For example, the pressure can be increased to generate a driving force that drives $C_{2+}$ compounds into the adsorbent medium. The pressure can be decreased to desorb the $C_{2+}$ compounds from the adsorbent medium. The PSA can function to preferentially adsorb or desorb one or more species over other species. For example, the adsorbent medium can be selected such that, with a pressure change, $C_{2+}$ compounds are adsorbed into, or desorbed from, the adsorbent medium, while other species, such non-$C_{2+}$ compounds (e.g., N2, $O_2$, $H_2O$), do not adsorb into or desorb from the adsorbent medium.

In some examples, a product stream from an OCM reactor is directed into a PSA unit at a first pressure (P1). Next, the pressure is changed from the first pressure to a second pressure (P2) to selectively separate $C_{2+}$ compounds in the product stream from non-$C_{2+}$ compounds. The pressure can be selected such that the ratio between the first pressure and the second pressure (P2/P1) is at least about 2, 3, 4, 5, 6, 7, 8, 9, 10, 20, 30, 40, 50, 60, 70, 80, 90, 100, 1000, 10,000, or 100,000.

Next, $C_{2+}$ compounds are recovered from the vessel. The $C_{2+}$ compounds can comprise ethane, ethylene, propane, propylene, butane, or higher carbon hydrocarbons, or any combination thereof. In some examples, the $C_{2+}$ compounds are $C_{2-5}$ compounds.

In an aspect, a method for recovering hydrocarbons having two or more carbon atoms ($C_{2+}$) from an oxidative coupling of methane (OCM) process comprises drying a product gas from an OCM reactor, performing a pressure swing adsorption (PSA) to separate $C_{2+}$ from methane and impurities, separating methane from the impurities, and returning the methane to the OCM reactor.

Figure 6:
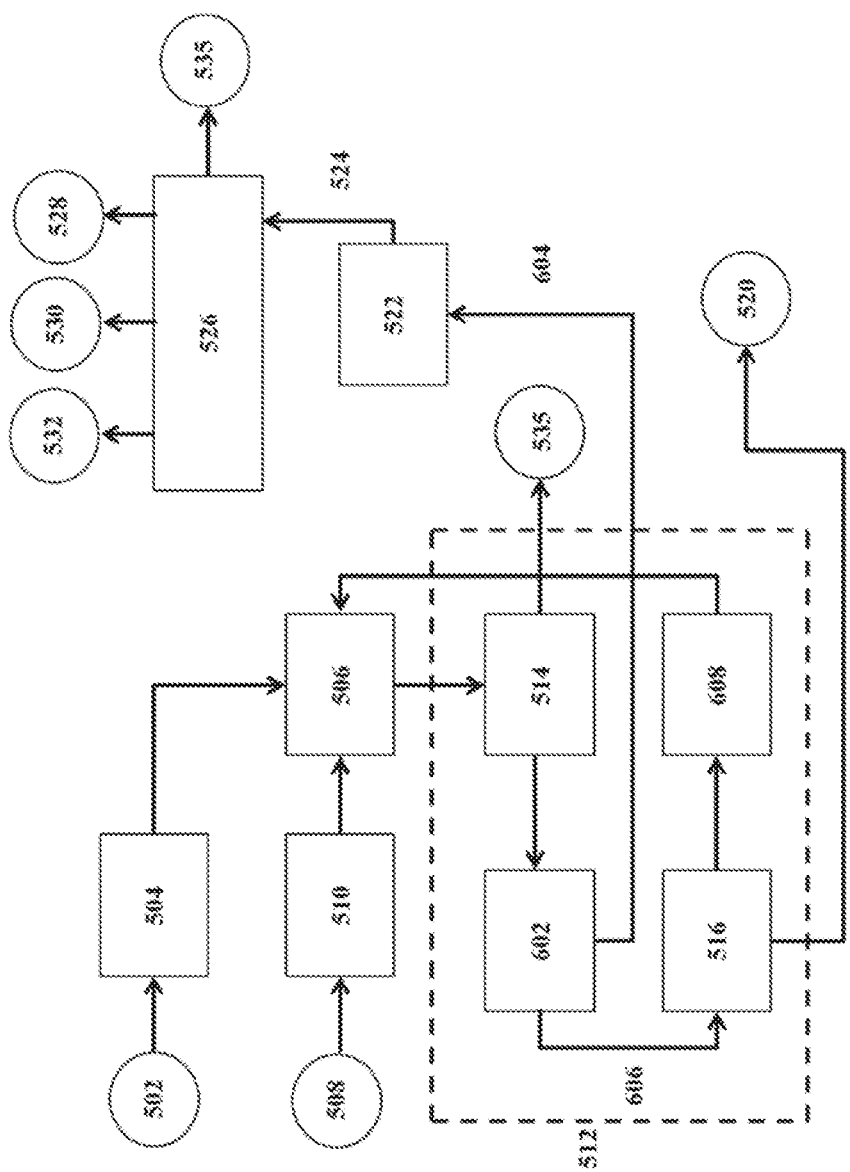
FIG. 6 provides a schematic illustration of an OCM process having a separations module comprising a $C_{2+}$ bed and/or pressure swing adsorber.

An example of a process is shown in FIG. 6, where like numbered elements represent like equipment and/or material flows compared with FIG. 5, the separations module can include a $C_{2+}$ bed 602. The $C_{2+}$ bed can be a separation and/or concentration bed. In some cases, the $C_{2+}$ bed is a pressure swing adsorption unit (PSA).

In some instances, the $C_{2+}$ bed recovers a high proportion of the $C_{2+}$ compounds that are produced in the OCM reactor 506. For example, the $C_{2+}$ bed can recover about 75%, about 80%, about 85%, about 90%, about 95%, about 97%, about 99%, about 95.5%, or about 99.9% of the $C_{2+}$ compounds that are produced in the OCM reactor. In some cases, the $C_{2+}$ bed recovers at least about 75%, at least about 80%, at least about 85%, at least about 90%, at least about 95%, at least about 97%, at least about 99%, at least about 95.5%, or at least about 99.9% of the $C_{2+}$ compounds that are produced in the OCM reactor.

In some cases, the $C_{2+}$ bed recovers the $C_{2+}$ compounds at a high concentration. For example, the stream enriched in $C_{2+}$ compounds can comprise about 20%, about 30%, about 40%, about 50%, about 60%, about 70%, about 80%, about 90%, or about 95% $C_{2+}$ compounds by mass. In some instances, the stream enriched in $C_{2+}$ compounds can comprise at least about 20%, at least about 30%, at least about 40%, at least about 50%, at least about 60%, at least about 70%, at least about 80%, at least about 90%, or at least about 95% $C_{2+}$ compounds by mass.

The stream comprising the recovered $C_{2+}$ compounds 604 can be fed to a compressor 522 and refrigeration unit 526 for fractionation as described herein. The stream depleted in $C_{2+}$ compounds 606 can be fed to the nitrogen recovery unit (NRU) as described herein. As shown in FIG. 6, the NRU 516 can recover the un-reacted methane and feed it into a compressor 608. The compressor can increase the pressure to any suitable pressure (e.g., the pressure of the OCM reactor 506). In some cases, the compressor increases the pressure by about 10 to 20 pounds per square inch. The compressed methane can be recycled to the OCM reactor 506.

Inclusion of a $C_{2+}$ bed 602 in the separations module 512 can further reduce the size and/or reduce the energy requirements of the refrigeration unit 526 (i.e., the refrigeration unit shown in FIG. 6 can be smaller and/or require less energy than the refrigeration unit as shown in FIG. 5). The further reduction in refrigeration size and/or energy requirement can be the result of removing the un-reacted methane from the enriched $C_{2+}$ stream 604 and/or removing most (e.g., at least 80%, at least 90%, or at least 95%) of the impurities and/or inert compounds from the enriched $C_{2+}$ stream 604.

In some cases, the refrigeration unit is about 0.5%, about 1%, about 2%, about 3%, about 4%, about 5%, about 6%, about 7%, about 8%, about 10%, about 12%, about 15%, or about 20% of the size as would be required in the absence of the separations module. In some cases, the refrigeration unit is less than about 0.5%, less than about 1%, less than about 2%, less than about 3%, less than about 4%, less than about 5%, less than about 6%, less than about 7%, less than about 8%, less than about 10%, less than about 12%, less than about 15%, or less than about 20% of the size as would be required in the absence of the separations module. In some instances, the refrigeration unit is between about 2% and 5% of the size as would be required in the absence of the separations module.

In some cases, the refrigeration unit requires about 0.5%, about 1%, about 2%, about 3%, about 4%, about 5%, about 6%, about 7%, about 8%, about 10%, about 12%, about 15%, or about 20% of the energy as would be required in the absence of the separations module. In some cases, the refrigeration unit requires less than about 0.5%, less than about 1%, less than about 2%, less than about 3%, less than about 4%, less than about 5%, less than about 6%, less than about 7%, less than about 8%, less than about 10%, less than about 12%, less than about 15%, or less than about 20% of the energy as would be required in the absence of the separations module.

In some cases, the separation does not result in a completely purified product stream. The composition of the OCM product stream can be adjusted using the separations described herein. In some cases, the OCM product stream is adjusted to more closely match the composition of the hydrocarbon process stream into which the OCM product stream is integrated.

In an aspect, a method for integrating an oxidative coupling of methane (OCM) process with a hydrocarbon process comprises performing an OCM reaction on a feed stream comprising methane to produce a product stream comprising $C_{2+}$ compounds, performing a separation on the product stream to produce an enriched stream and flowing the enriched stream into a hydrocarbon process. The hydrocarbon process can be without limitation, an oil refinery, a natural gas liquids (NGL) process, or a cracker.

In some cases, the enriched stream does not include purified $C_{2+}$ compounds. That is, the concentration of $C_{2+}$ compounds can be about 10%, about 20%, about 30%, about 40%, about 50%, about 60%, about 70%, about 80%, or about 90% by mass. In some cases, the concentration of $C_{2+}$ compounds is less than about 10%, less than about 20%, less than about 30%, less than about 40%, less than about 50%, less than about 60%, less than about 70%, less than about 80%, or less than about 90% by mass.

The enriched stream can be relatively more enriched in $C_{2+}$ compounds than the OCM product stream. In some cases, the ratio of the concentration of $C_{2+}$ compounds in the enriched stream to the OCM product stream is about 1.1, about 1.3, about 1.5, about 2, about 3, about 3.5, about 4, about 4.5, about 5, about 6, about 8, about 10, about 15, about 20, or about 50. In some instances, the ratio of the concentration of $C_{2+}$ compounds in the enriched stream to the OCM product stream is at least about 1.1, at least about 1.3, at least about 1.5, at least about 2, at least about 3, at least about 3.5, at least about 4, at least about 4.5, at least about 5, at least about 6, at least about 8, at least about 10, at least about 15, at least about 20, or at least about 50.

The rough-cut separation can be used to approximately match the composition of the OCM product stream to the composition of the hydrocarbon stream into which it is integrated. Performing the rough-cut separation can make it so that the operating parameters of the hydrocarbon process do not need to be adjusted when being integrated with OCM. The OCM product stream can include various $C_{2+}$ compounds, impurities, inert components, and un-reacted methane, the concentration of any combination of which can be approximately matched to the concentration of the hydrocarbon stream into which the OCM product stream is integrated. In some cases, one or more of the concentrations are matched to about 0.5%, about 1%, about 2%, about 5%, about 7%, about 10%, about 15%, about 20%, about 30%, about 40%, or about 50%. In some cases, one or more of the concentrations are matched to within at most 0.5%, within at most 1%, within at most 2%, within at most 5%, within at most 7%, within at most 10%, within at most 15%, within at most 20%, within at most 30%, within at most 40%, or within at most 50%.

In some cases, the OCM reaction is performed at an inlet temperature between 400° C. and 600° C. The method can also include flowing the enriched stream into a hydrocarbon process such as an oil refinery, a natural gas liquids (NGL) process, or a cracker.

In an aspect, a method for integrating an oxidative coupling of methane (OCM) process with a hydrocarbon process comprises performing an OCM reaction on a feed stream comprising methane to produce a product stream comprising $C_{2+}$ compounds, performing a separation on the product stream to enrich $C_{2+}$ compounds, thereby producing an enriched stream; and flowing the enriched stream into a hydrocarbon process at a point in the hydrocarbon process where the concentration of $C_{2+}$ compounds is approximately matched to the concentration of $C_{2+}$ compounds in the enriched stream. In some cases, the hydrocarbon process is an oil refinery, a natural gas liquids (NGL) process, or a cracker.

In an aspect, a method for integrating an oxidative coupling of methane (OCM) process with a hydrocarbon process comprises performing an OCM reaction on a feed stream comprising methane to produce a product stream comprising $C_{2+}$ compounds and impurities, performing a separation on the product stream to deplete impurities, thereby producing an impurity-depleted stream; and flowing the impurity-depleted stream into a hydrocarbon process at a point in the hydrocarbon process where the concentration of the impurities is less than 10% different than the concentration of the impurities in the impurity-depleted stream. In some cases, the hydrocarbon process is an oil refinery, a natural gas liquids (NGL) process, or a cracker.

Integration with a Refinery

An oil refinery or petroleum refinery is an industrial process plant where crude oil is processed and refined into more useful products such as petroleum naphtha, gasoline, diesel fuel, asphalt base, heating oil, kerosene, and liquefied petroleum gas. Oil refineries are typically large, sprawling industrial complexes with extensive piping running throughout, carrying streams of fluids between large chemical processing units. In many ways, oil refineries use much of the technology of, and can be thought of, as types of chemical plants. The crude oil feedstock has typically been processed by an oil production plant. There is usually an oil depot (tank farm) at or near an oil refinery for the storage of incoming crude oil feedstock as well as bulk liquid products.

The OCM process can be integrated with an oil refinery in any suitable way, such as drawing from any stream having methane, flowing $C_{2+}$ compounds into the refinery at any stream location having or able to accept $C_{2+}$ compounds, and/or transferring heat between the OCM process and the oil refinery.

In some cases, the refinery produces "off gas" comprising methane that can be converted to $C_{2+}$ compounds in an OCM process. In some cases, the off gas is burned either within the furnaces or other systems of a processing facility, e.g., for heat generation, or it may be burned for no purpose other than disposal (flared) in the oil refinery. Integrating an oil refinery with an OCM process provides a way for the oil refinery to recoup additional value from its petroleum feedstock, by recapturing values from what is typically considered a waste gas or low value component, e.g., fuel gas.

Figure 7:
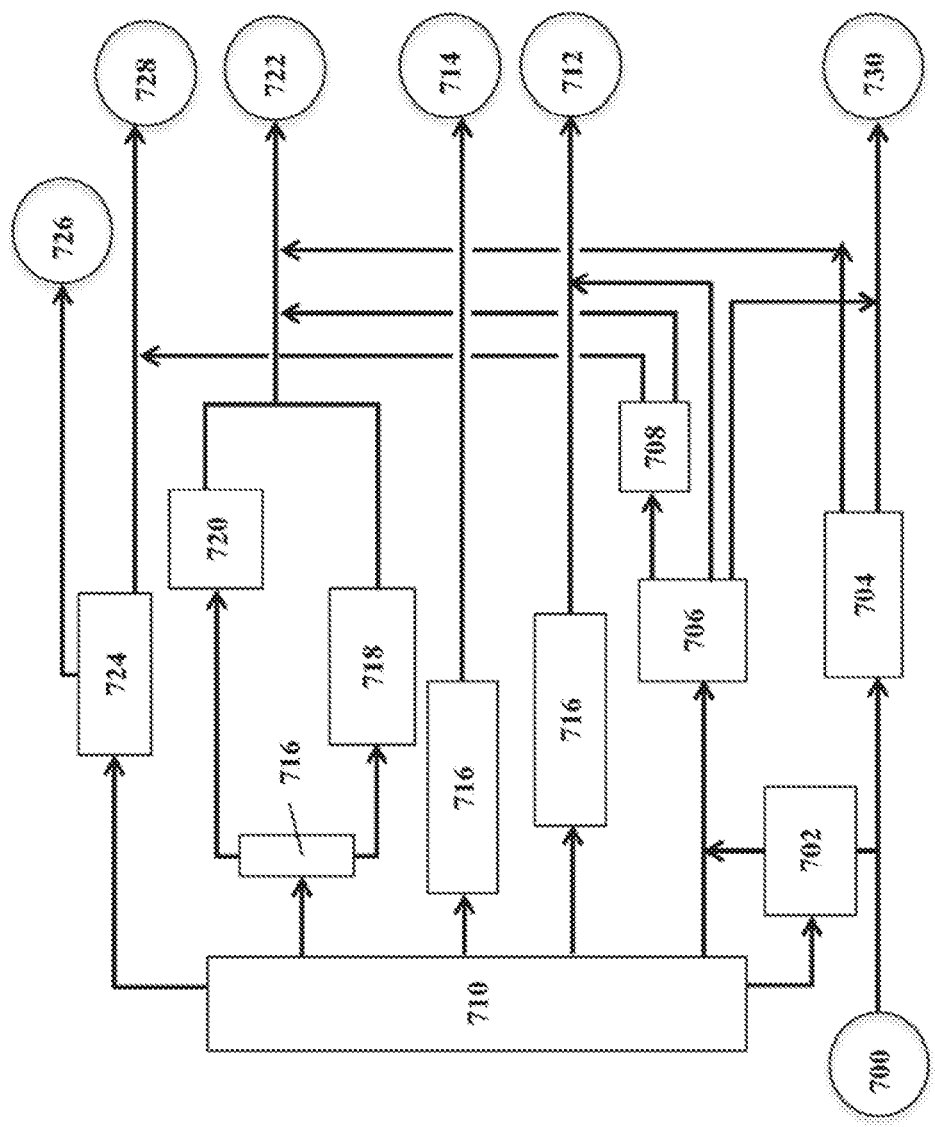
FIG. 7 provides a schematic illustration of an example of a refinery.

FIG. 7 shows a schematic drawing of an oil refinery. Additional details can be found in "Petroleum Refining in Nontechnical Language, $4^{th}$ Edition" by William Leffler published Nov. 13, 2008, which is incorporated herein by reference in its entirety. As shown, petroleum feedstock 700 can be split between a flasher 702 and a visbreaker 704. The flasher can feed the visbreaker and a catalytic cracking unit (CCU) 706. The visbreaker can reduce the quantity of residual oil produced in the distillation of crude oil and increase the yield of middle distillates (e.g., by thermally cracking large hydrocarbon molecules by heating in a furnace to reduce viscosity and produce small quantities of light hydrocarbons). The CCU can convert high molecular weight hydrocarbon fractions (e.g., molecular weight from about 200 to 600 grams/mole) to lower molecular weight gasoline, olefinic gases, and other products. In some cases, the CCU is a fluid catalytic cracker accepting material having an initial boiling point of 340° C. or higher. A portion of the material from the CCU can be fed to an alkylation unit 708. In some cases, the alkylation unit converts isobutene and low molecular weight alkenes (e.g., propene and butene) in the presence of a strong acid catalyst. The refinery can also produce residual fuel 730.

Material entering the distillation unit 710 can be derived from petroleum 700 or derivatives thereof. High molecular weight compounds from a distillation unit 710 can also be fed to the CCU. Middle boiling compounds can be taken off as various fractions to be converted to distillate fuel 712 and jet fuel 714 for example. In some cases, the fractions are hydrotreated 716 (e.g., to remove sulfur). FIG. 7 shows two hydrotreaters 716 (i.e., one for the distillate fuel 712 and one for the jet fuel 714), but any number are possible. Compounds boiling at a lower temperature in the distillation column can be fed to a splitter 716 which divides the incoming flow between a reformer 718 and an isomerizer 720. In some cases, the reformer, also known as a catalytic reformer, converts naptha typically having low octane rating into high-ocatane liquid products called reformates, a component of gasoline 722. In some cases, the isomerizer converts linear molecules to higher-octane branched molecules for blending into gasoline or feed to alkylation units.

Gases from the distillation unit(s) 710 can be fed into a gas plant 724. The gas plant can produce, amongst other things, sulfur 726 and fuel gas 728.

Figure 8:
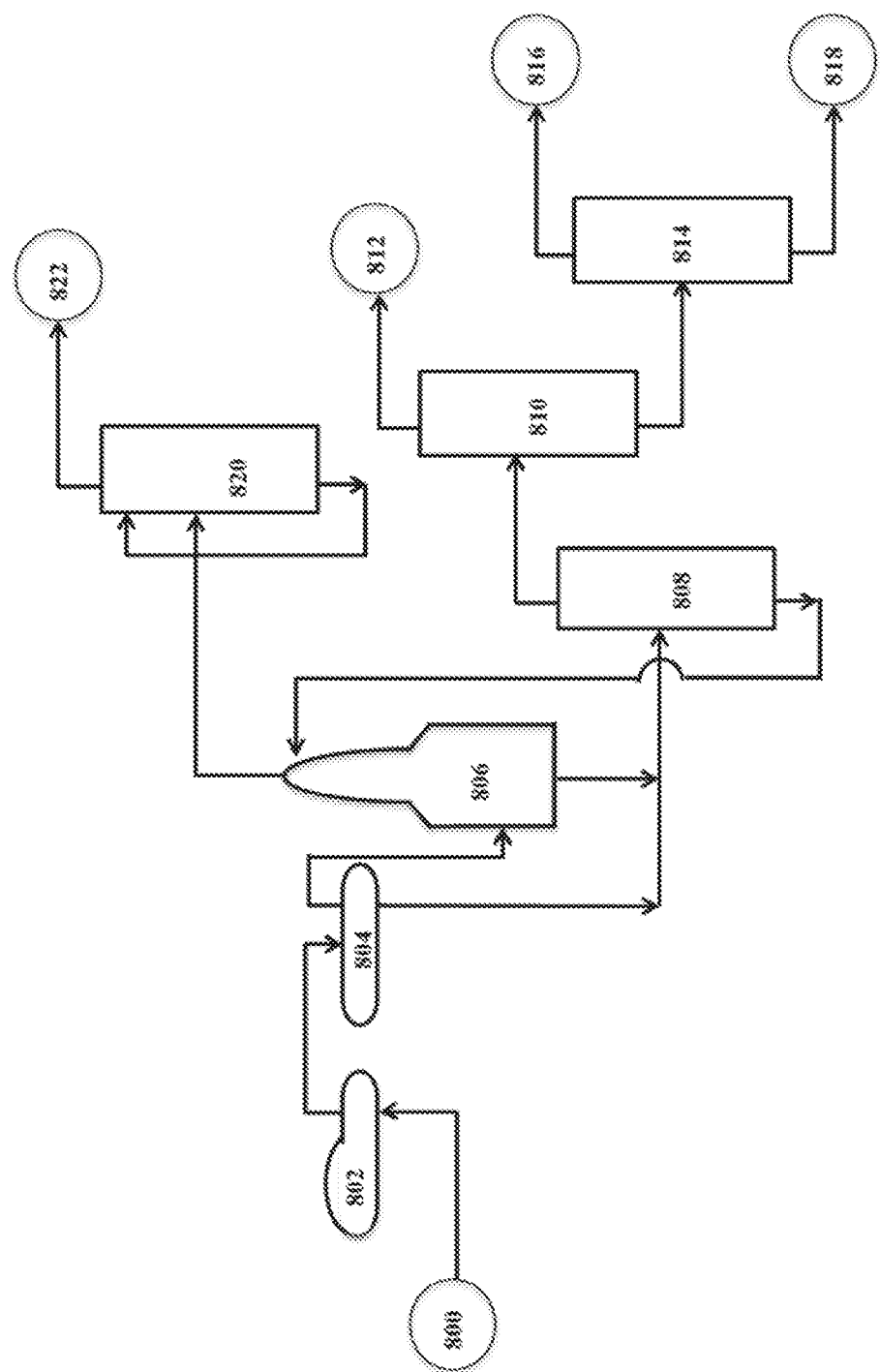
FIG. 8 provides a schematic illustration of an example of a gas plant.

FIG. 8 shows a schematic drawing of a representative gas plant 724. Gas 800 can be fed into a compressor 802 followed by a phase separator 804. The phases from the phase separator can be split between an absorber 806 and a de-butanizer 808. Some material from the de-butanizer can be returned to the absorber 806 and some can be flowed onto a de-propanizer 810. The de-propanizer can produce a propane fraction 812 and flow the butanes on to a de-isobutanizer 814. The de-isobutanizer can split the incoming butane stream into iso-butane 816 and n-butane 818 fractions. The absorber 806 can also flow smaller molecular weight gases ($C_{2-}$) to a sponge absorber 820. In some embodiments, the $C_{2-}$ gases 822 are integrated with an OCM or ODH process as described herein.

Figure 9:
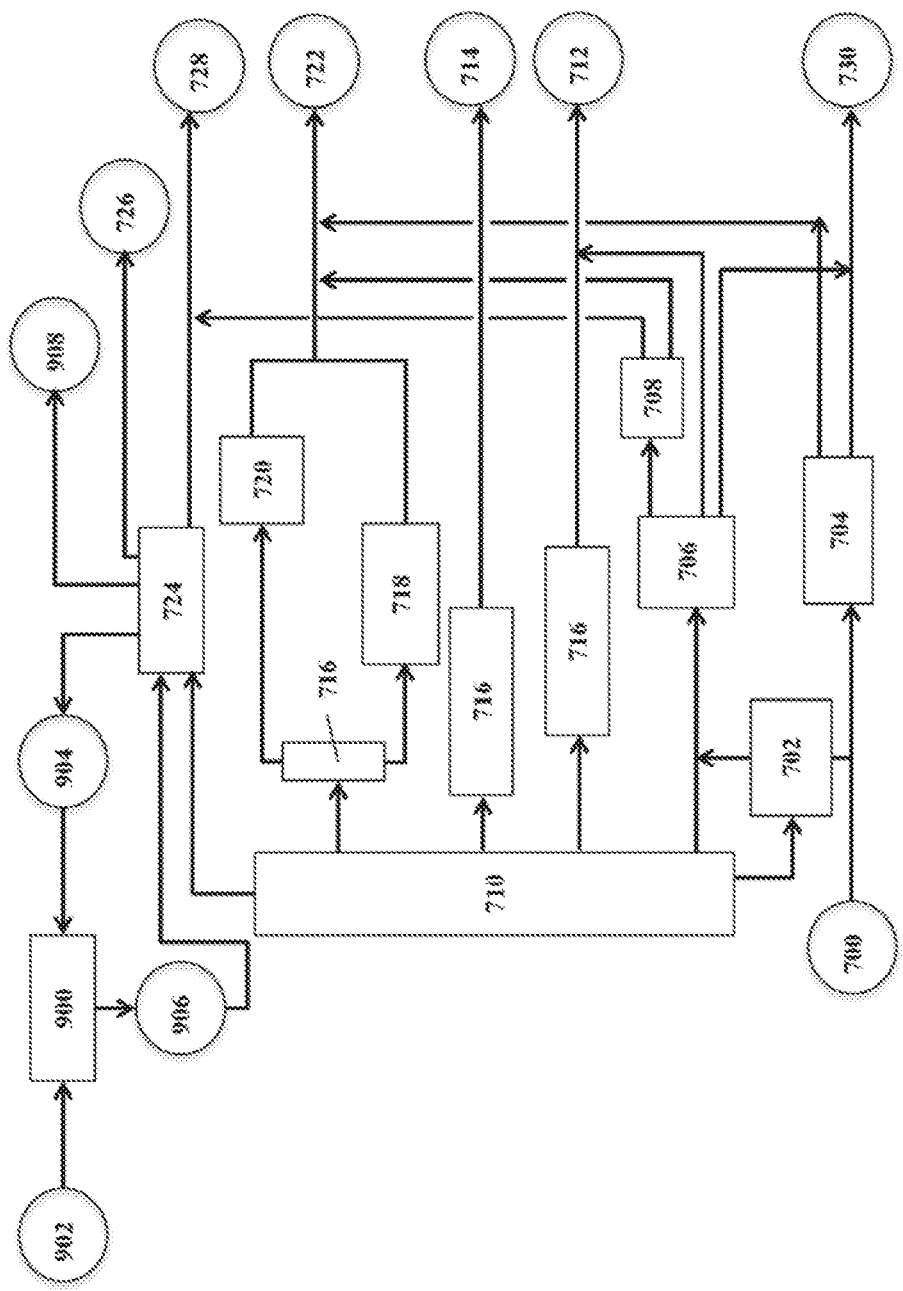
FIG. 9 provides a schematic illustration of an example of integrating an OCM process with a refinery.
Figure 10:
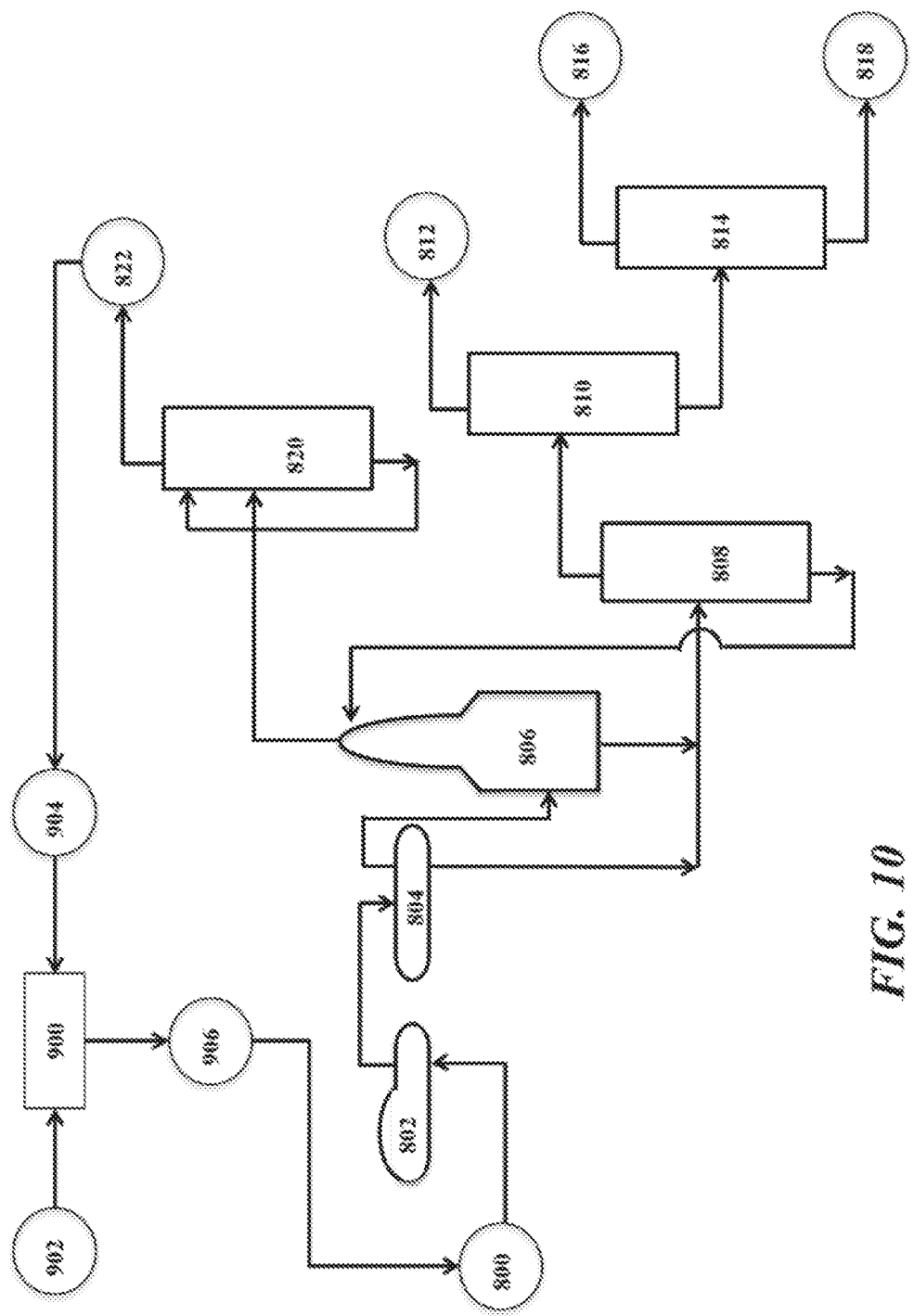
FIG. 10 provides a schematic illustration of an example of integrating an OCM process with a gas plant.

FIG. 9 shows an example of the integration of an OCM process 900 with the gas plant 724 of a refinery. Methane can be drawn from geological and/or biological sources 902 (e.g., natural gas) and/or from the gas plant 904 or other suitable portion of the refinery. In some cases, the OCM product 906 is fed into the gas plant 724 where it can be separated into one or more fractions. In some cases, separations are performed before the OCM product is flowed into the gas plant (not shown). In some cases, carbon dioxide from the gas plant 908 is used in enhanced oil recovery (EOR). FIG. 10 shows an example of the integration of an OCM process with the gas plant in more detail where like numbered elements are the same as those described in FIGS. 8 and 9.

Figure 11:
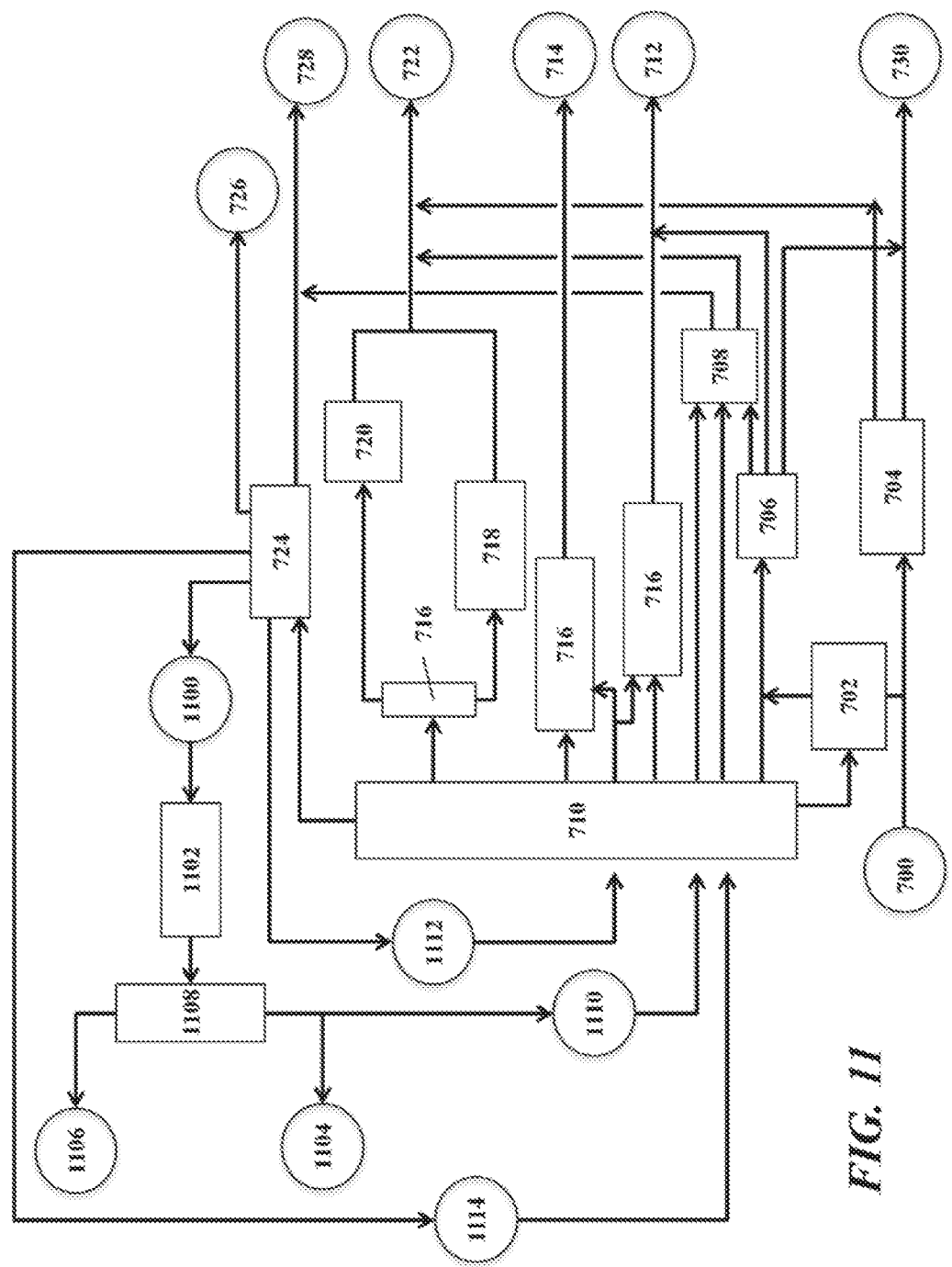
FIG. 11 provides a schematic illustration of an example of integrating an oxidative dehydrogenation of ethane to ethylene or propane to propylene (ODH) process with a refinery.

In some embodiments, the OCM, ODH, and/or ethylene to liquids ("ETL") processes described herein are integrated with a refinery. FIG. 11 shows additional examples of such integration with the gas plant 724. Propane 1100 can be drawn off of the gas plant and put through an ODH process 1102 to produce propylene. The propylene 1104 can be separated from un-reacted propane 1106 in a separator 1108. Unreacted propane stream 1106 can alternatively be fed back into the ODH reactor 1102. Unreacted propane stream 1106 can alternatively be used as a diluent to the ETL reactor (not shown). Some of the propylene 1110 can be fed into the alkylation unit 708. In some instances, an ETL reactor (not shown) can produce butane (e.g., iso-butane, n-butane, or a combination thereof) that can be fed into the alkylation unit 708. In some cases, the amount of propylene fed into the alkylation unit is greater than would be the case in the absence of OCM, ODH, and/or ETL integration. Alternatively, if the OCM effluent undergoes separations in lieu of a gas plant as described previously, the hydrogen that is separated can be fed into the hydrotreating units 716.

In some instances, the OCM, ODH, and/or ETL processes produce gases (e.g., products, co-products, un-reacted gases, and/or gases introduced from the air used as an oxygen source). These gases can be separated in the gas plant. As shown in FIG. 11, hydrogen ($H_2$) from the gas plant 1112 can be fed into one or more hydrotreating units 716. In some instances, the hydrogen is a larger quantity of hydrogen than would be present in the absence of OCM, ODH, and/or ETL integration.

Figure 12:
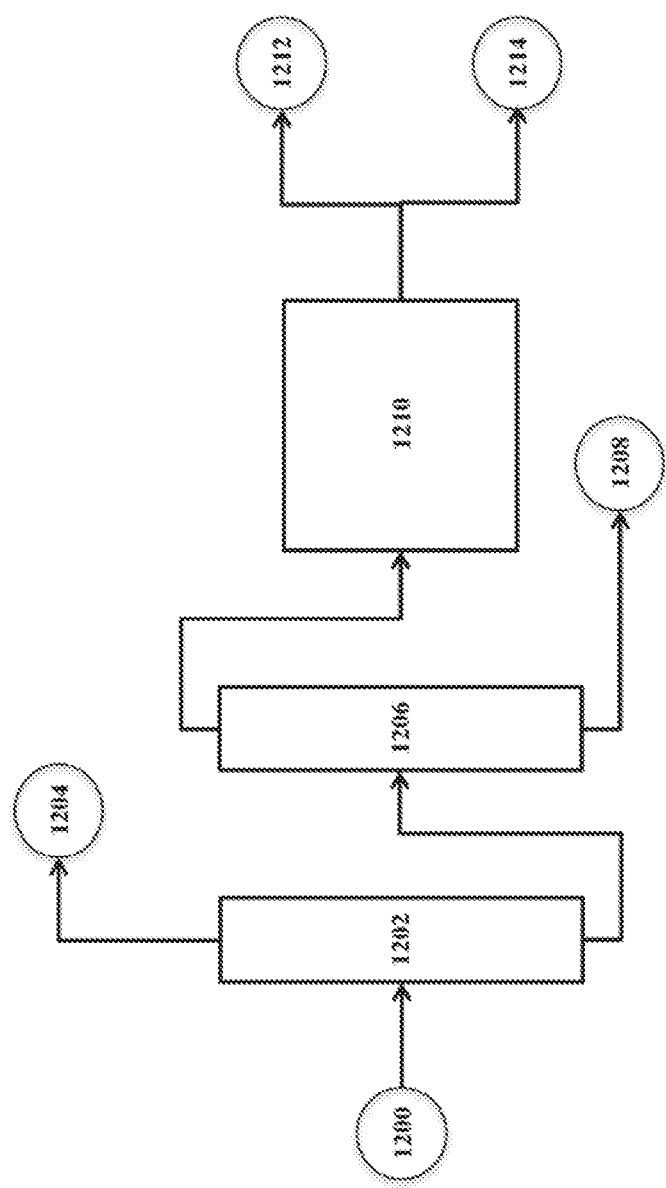
FIG. 12 provides a schematic illustration of an example an aromatics recovery unit.

As described herein, refineries can produce a mixture of aromatic hydrocarbons generally known as BTX. FIG. 12 shows an example of an aromatics recovery unit, which is a process for the recovery of BTX from a refinery. Hydrocarbons having BTX 1200 (e.g., straight run gasoline and/or reformate) can be fed into a first separations unit 1202 that removes hydrocarbons that are lighter than benzene (i.e., have a lower molecular weight and/or lower boiling point) 1204. The remaining material can be fed into a second separations unit 1206 that removes hydrocarbons that are heavier than toluene (i.e., have a higher molecular weight and/or higher boiling point) 1208. The remaining material from the second separations unit (e.g., known as a "heart cut" and comprises aromatics concentrate) can be fed into an aromatics recovery unit 1210. The aromatics recovery unit 1210 can separate the heart cut into BTX 1212 and raffinate 1214. In some instances, raffinate is an acceptable gasoline blending component.

Figure 13:
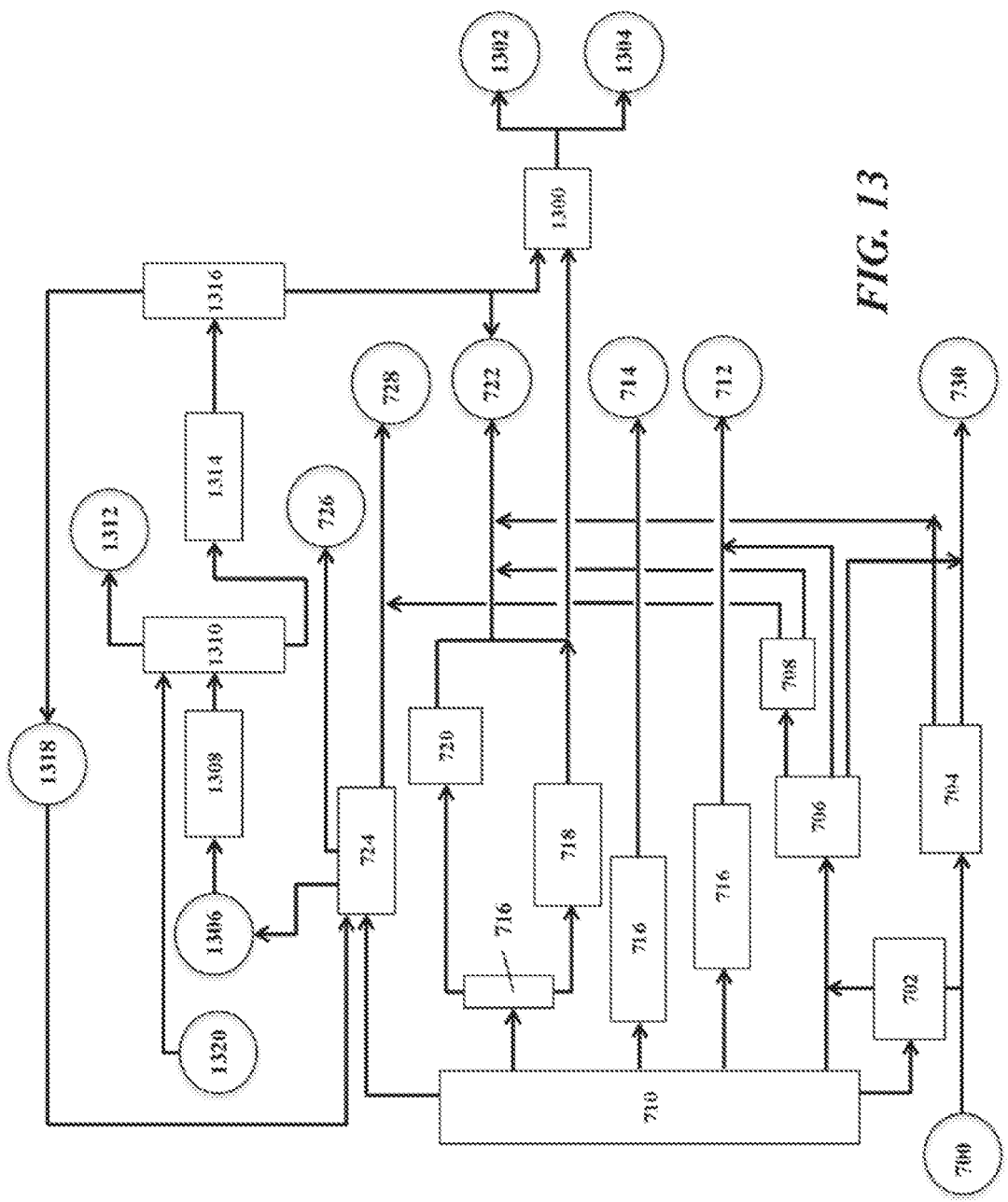
FIG. 13 provides a schematic illustration of an example of integrating an ODH and ethylene to liquids (ETL) process with a refinery.

In some embodiments, the ethylene to liquids ("ETL"), or OCM and ETL, and/or ODH and ETL processes described herein are integrated with a refinery (e.g., a refinery having an aromatics recovery unit). FIG. 13 shows a refinery with an aromatics recovery unit 1300 for the production of BTX 1302 (with raffinate co-product 1304 that is for example suitable for blending with gasoline). In some embodiments, the aromatics recovery unit is supplemented with hydrocarbons from an integrated OCM, ODH, and/or ETL processes.

As shown in FIG. 13, ethane 1306 can be withdrawn from the gas plant 724 and converted to ethylene in an ODH reactor 1308. A separations module 1310 can separate the ethylene from un-reacted ethane 1312. In some cases, additional ethylene 1320 is provided to the separations module 1310. The ethylene can be fed into an ethylene to liquids (ETL) process 1314 for conversion into higher molecular weight hydrocarbons ($C_{2+}$). The higher molecular weight hydrocarbons can be transferred to an ETL separations unit 1316 where propane and butane 1318 are optionally returned to the gas plant or alkylation unit. Other fractions from the ETL separations unit can be blended with gasoline 722 or fed into the aromatics recovery unit 1300.

Exothermic reactions can occur in one or more of OCM, ODH and ETL units. The reaction heat may be recovered to produce steam, a portion of which may be used to provide heat to or to generate power for the OCM, ODH and ETL units themselves. The remaining portion of steam may be fed to the refinery plant or may be used to generate power that is exported outside the OCM, ODH and ETL units' battery limits.

The various figures showing integration with a refinery are illustrative and not limiting. Additional embodiments can be readily generated by combining the examples shown in FIGS. 7 to 13. In some instances, thermal energy and/or electricity are integrated with the refinery (e.g., heat from an exothermic OCM reaction can be transferred to any place in the refinery requiring heat).

Integration with Natural Gas Processing

As compared to crude oil, natural gas is currently in relatively abundant supply, particularly in accessible and available locations, such as in North America. When viewed at a national level, the gas reserves within the United States are currently among the largest in the world, providing not only a highly valued natural resource, but also providing the potential for greater energy independence for the country. Exploitation of those reserves, however, can pose challenges distinct from those faced and managed by the oil industry. In some cases, large-scale transport of natural gas is typically accomplished by pipeline, which can create expensive infrastructure requirements. Long-distance gas pipelines generally require consistent and predictable qualities of gas in order to function economically and safely. For example, the energy density and vapor pressure of the gas to be moved long distance is generally required to fall within a predetermined specification. As a result, the gas industry has resorted to building processing facilities close to gas fields at which raw incoming natural gas containing impurities such as $CO_2$, $N_2$, water, regulated compounds such as heavy metals, and valuable components including $C_1$, $C_2$, $C_3$, $C_4$, and $C_5+$ are separated into more manageable gases and liquids that can, for example, be transported by less costly and more appropriate means, e.g., common-carrier pipeline, rail, truck, etc.

These facilities typically take in natural gas, which is, depending upon the source of the gas, typically comprised of a mixture of varying amounts of methane, higher hydrocarbons (e.g., $C_{2+}$), water vapor, hydrogen sulfide ($H_2S$), carbon dioxide, helium, nitrogen, and other compounds.

Natural gas processing typically involves separating the various impurities, higher hydrocarbons and fluids from the gas, to produce what is generally known as "pipeline quality" dry natural gas. Major transportation pipelines usually impose restrictions on the make-up of the natural gas that is allowed into the pipeline. That means that before the natural gas can be transported it must be appropriately treated to meet the requirements of the pipeline. The ethane, propane, butane, pentanes and other higher hydrocarbons that are removed from this natural gas are generally known as "natural gas liquids" (NGLs). NGLs can be valuable by-products of natural gas processing, and are therefore also typically recovered in these facilities. NGLs can include ethane, propane, butane, iso-butane, and natural gasoline. These NGLs are generally sold separately from the pipeline ready gas, and can have a variety of different uses; including providing raw materials for oil refineries or petrochemical plants, and as sources of energy, while other separated components are used in other applications, e.g., for enhancing oil recovery.

While some of the needed processing can be accomplished at or near the gas wellhead (field processing), as noted herein, the complete processing of natural gas typically takes place at one or more processing plants that are usually located within the natural gas producing region. The extracted natural gas can be transported to these processing plants through a network of gathering pipelines, which are generally small-diameter, low-pressure pipes. A complex gathering system can include thousands of miles of pipes, interconnecting the processing plant to upwards of 100 wells in the area.

In addition to processing done at the wellhead and at centralized processing plants, some additional processing is also sometimes accomplished at "straddle extraction plants". These plants are typically located on major pipeline systems. Although the natural gas that arrives at these straddle extraction plants is typically already of pipeline quality, in some instances there may still exist small quantities of NGLs or other impurities, which can be extracted at the straddle plants.

The practice of processing natural gas to pipeline dry gas quality levels can be quite complex, but usually involves four main processes to remove the various impurities: oil and condensate removal, water removal, glycol dehydration and solid desiccant dehydration. In addition to these four processes, heaters and scrubbers are often installed, usually at or near the wellhead. The scrubbers serve primarily to remove sand and other large-particle impurities. The heaters can ensure that the temperature of the gas does not drop too low (e.g., such that undesired condensation of water takes place). With natural gas that contains even low quantities of water, natural gas hydrates can have a tendency to form when temperatures drop. These hydrates are typically solid or semi-solid compounds, resembling ice like crystals, and their accumulation can impede the passage of natural gas through valves and gathering systems. To reduce the occurrence of hydrates, small natural gas-fired heating units are typically installed along the gathering pipe wherever hydrates may form.

As noted herein, natural gas coming directly from a well can contain many natural gas liquids that are commonly removed. Most NGLs are removed to meet common carried pipeline specifications, often referred to as required extraction. When Natural gas liquids (NGLs) have sufficiently high economic values as separate products, it can become economical to remove more than the minimum amount of NGLs contained in the gas stream, a scenario often referred to as discretionary extraction. The removal of natural gas liquids usually takes place in a relatively centralized processing plant, and uses techniques similar to those used to dehydrate natural gas. There are generally two basic steps to the treatment of natural gas liquids in the natural gas stream. First, the liquids are extracted from the natural gas. Second, these natural gas liquids are separated themselves, down to their base or more pure components.

Integration with NGL Extraction

The NGLs can initially be extracted from the natural gas stream. In typical gas processing, there are two principle techniques for removing NGLs from the natural gas stream: the absorption method and the cryogenic expander process, also referred to as a cryogenic extraction or separation process. According to the Gas Processors Association, these two processes currently account for around 90% of total natural gas liquids production.

In NGL absorption, an absorbing oil that has an affinity for NGLs is typically used in much the same manner as glycol (which has an affinity for water when used in the dehydration process). Before the absorbing oil has picked up any NGLs, it is generally termed "lean" absorption oil. In some cases, as the natural gas is passed through an absorption tower, it is brought into contact with the absorption oil, which soaks up, or absorbs, a high proportion of the NGLs. The "rich" absorption oil, now containing NGLs, can exit the absorption tower through the bottom. It is now typically a mixture of absorption oil, propane, butanes, pentanes, and other heavier hydrocarbons. The rich oil can be fed into lean oil stills, where the mixture can be heated to a temperature above the boiling point of the NGLs, but below that of the oil. This process generally allows for the recovery of around 75% of butanes, and 85 to 90% of pentanes and heavier hydrocarbons from the natural gas stream.

The basic absorption process described above can be modified to improve its effectiveness, or to target the extraction of specific NGLs for example. In the refrigerated oil absorption method, where the lean oil is cooled through refrigeration, propane recovery can be greater than 90% in some cases, and around 40% of ethane can be extracted from the natural gas stream in some cases. Extraction of the other, heavier NGLs can be close to 100% using this process (e.g., at least 90%, at least 95%, at least 99%, or at least 99.9%).

Cryogenic extraction processes can also be used to extract NGLs from natural gas, and are more commonly used today. While absorption methods can extract almost all of the heavier NGLs (e.g., at least 95%), the lighter hydrocarbons, such as ethane, are often more difficult to recover from the natural gas stream. In some instances, it is economic to simply leave the lighter NGLs in the natural gas stream. However, if it is economic to extract ethane and other lighter hydrocarbons, cryogenic processes can be used for high recovery rates. In some cases, cryogenic processes include dropping the temperature of the gas stream to around negative 120 degrees Fahrenheit. In some instances, the condensed NGLs are then transported to subsequent processes while the gas components (e.g., methane and nitrogen and other gases) are taken off in gas form.

In some cases, the extraction systems used herein operate both to separate non-hydrocarbon compounds, such as $CO_2$, $N_2$, and water from the hydrocarbon compounds, e.g., NGLs, but also function to de-methanize the gas stream (e.g., separating methane from higher hydrocarbons and NGLs). As such, the extraction units can separate one or more non-hydrocarbon compounds from one or more hydrocarbon compounds, or, when functioning as a de-methanizing unit, can separate at least one hydrocarbon component, i.e., methane, from at least one other hydrocarbon component, i.e., $C_2+$ compounds.

There can be a number of different ways of chilling the gas to these temperatures, but the turbo expander process is generally most effective. In this process, external refrigerants can be used to cool the natural gas stream. Then, an expansion turbine can be used to rapidly expand the chilled gases, which can cause the temperature to drop significantly. This rapid temperature drop can condense ethane and other hydrocarbons in the gas stream, while maintaining methane in gaseous form. This process can allow for the recovery of about 90% to 95% of the ethane originally in the gas stream. In addition, the expansion turbine is generally able to convert some of the energy released when the natural gas stream is expanded into recompressing the gaseous methane effluent, thus saving energy costs associated with extracting ethane.

The extraction of NGLs from the natural gas stream can produce cleaner, purer natural gas, as well as enabling a more complete extraction of the valuable hydrocarbons that are the NGLs themselves (when compared with not extracting NGLs).

Integration with Natural Gas Liquid Fractionation

Once higher hydrocarbons, e.g., ethane and NGLs have been removed from the natural gas stream, they are typically broken down into their base components that can each have a separate value. The process that is typically used to accomplish this task is called fractionation. Fractionation processes typically operate based on the different boiling points of the different hydrocarbons in the NGL stream. In some cases, fractionation is carried out in the same facility as the earlier gas processing steps, e.g., dehydration, de-acidification and extraction/de-methanization, while in other cases, fractionation occurs in a separate facility to which the composite NGLs are delivered.

The entire fractionation process can be broken down into steps, starting with the removal of the lighter NGLs from the stream. In operation, fractionation can occur in stages where different hydrocarbons are boiled off, one by one, where the name of a particular fractionator reflects to its function, as it is conventionally named for the hydrocarbon that is boiled off. Accordingly, the process typically includes, in order, a de-ethanizer, which separates the ethane from the remaining NGL stream, a de-propanizer; which separates the propane from the remaining NGL stream, and a de-butanizer, which boils off the butanes. In some cases, the remaining stream then primarily contains the pentanes and heavier hydrocarbons in the NGL stream. The separated butanes are also typically passed through a butane splitter or de-isobutanizer, which can separate the iso and normal butanes. In some cases, the fractionation system, whether referred to in its entirety or with respect to individual fractionation units, e.g., a de-propanizer, typically operates to separate at least one hydrocarbon component such as propane, from at least one other different hydrocarbon component, such as butane, pentane, etc. In some cases, the separation is not entirely complete. For example, the de-ethanizer can remove less than 100% of the ethane from the remaining NGL stream. Likewise, subsequent individual fractionation units can remove less than 100% of their respective compounds. In general, these fractionation steps can remove a substantial amount and majority of the compound for which they are targeted, from the remaining NGL stream, e.g., greater than 50%, greater than 60%, greater than 75% and even greater than 90% or 95%.

Figure 14:
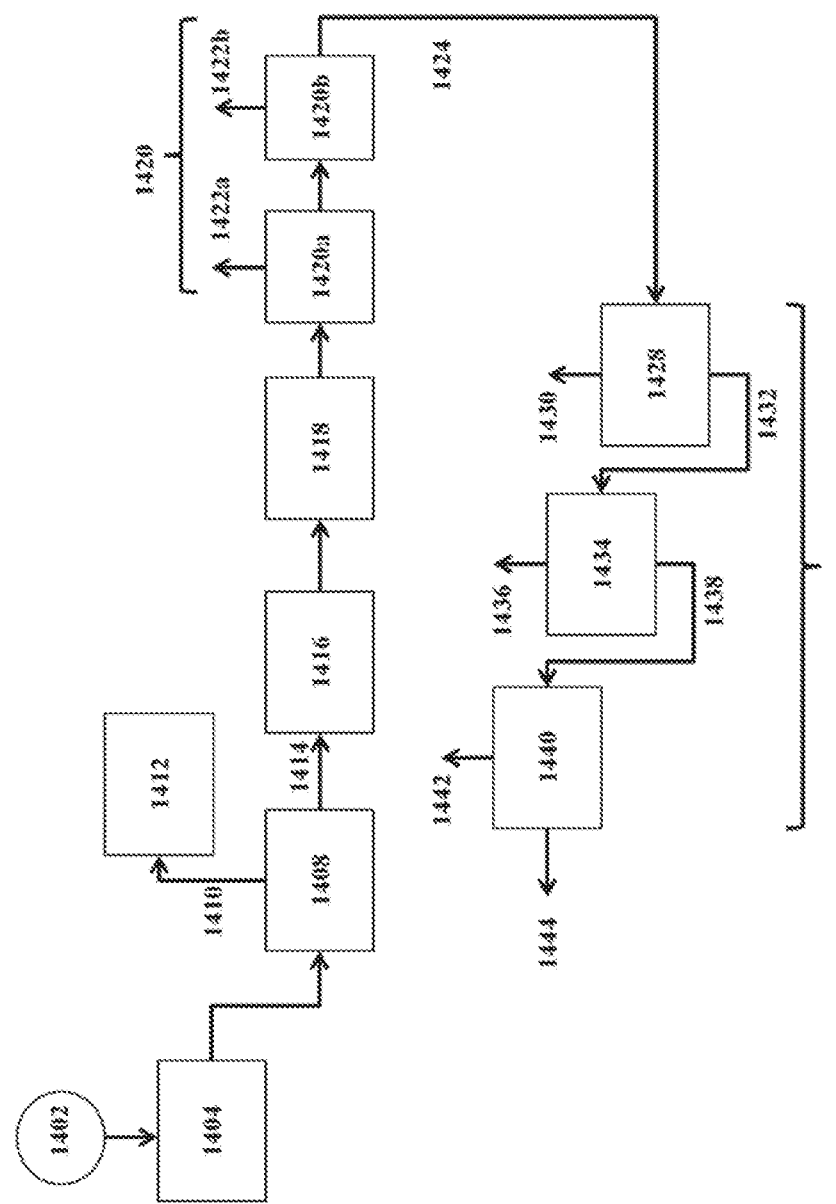
FIG. 14 schematically illustrates an example of a natural gas processing facility.

FIG. 14 provides a schematic illustration of major component processes and systems in a typical natural gas processing facility. As shown in this example, raw gas from the gas well or other source 1402, which may have been treated at the well or another intermediate processing unit or facility to remove water and other condensates, e.g., at step 1404, is transported to a processing facility. Incoming raw gas 1406 is then treated in an acid gas removal step/unit 1408, to remove any hydrogen sulfide or other corrosive gases 1410. The removed sulfur compounds or "acid gas" can be subjected to additional processing, e.g., in sulfur unit 1412, and additional processing to yield elemental sulfur and tail gases, which may be further processed and/or incinerated.

The de-acidified gas 1414 is then passed through a dehydration unit 1416 to remove further water, and then passed through one or more additional purification units 1418, e.g., for removal of other impurities, such as mercury. The purified natural gas is then passed into an extraction unit 1420, which may be a cryogenic extractor that comprises a cryogenic turbo expander unit 1420a and a cryogenic nitrogen rejection unit 1420b, for separation of methane in a methane rich stream 1422a, and nitrogen 1422b from the NGL stream 1424. The resulting methane rich component is then passed on as pipeline ready natural gas, e.g., transferred to the sales gas pipeline for market, or as discussed in greater detail herein, may be subjected to further processing. As noted herein, the extraction system 1420 optionally may include a lean oil extraction unit in place of a cryogenic extraction unit.

The resulting de-methanized NGL containing product 1424, including ethane and other higher hydrocarbons (generally referred to herein as $C_2+$ components), is then passed through a fractionation train 1426 that typically includes a de-ethanizer unit 1428 that boils off the $C_2$ hydrocarbons 1430 and passes the remaining fluids or "bottoms" 1432 to a de-propanizer unit 1434. The de-propanizer unit, in turn, boils off the $C_3$ gases 1436, and passes the remaining bottoms 1438 to a debutanizer unit 1440, which boils off butanes 1442, leaving pentanes and higher order hydrocarbons in stream 1444. Each of the higher hydrocarbon streams 1430, 1436, 1442 and 1444, may then be subjected to additional processing, e.g., through sweetening units or butane splitters.

Integration with Steam Cracking

As described herein, other significant petrochemical processing can revolve around the production of olefins and other higher hydrocarbons from natural gas, or petroleum distillates, like naphtha. In particular, saturated hydrocarbons can be processed or converted to unsaturated hydrocarbons through a process called steam cracking. In steam cracking, a gaseous or liquid hydrocarbon feed like naphtha, gas oil, liquefied petroleum gas ("LPG"), or ethane can be diluted with steam and briefly heated in a furnace without the presence of oxygen. Typically, the reaction temperature is very high, at around 850° C. or higher, but the reaction is only allowed to take place very briefly. In modern cracking furnaces, the residence time is reduced to milliseconds to improve yield, resulting in gas velocities faster than the speed of sound. In some cases, after the cracking temperature has been reached, the gas is quickly quenched to stop the reaction in a transfer line heat exchanger or inside a quenching header using quench oil. The resulting products are then further processed to separate distinct high value products, such as olefins, from undesirable by-products and un-reacted feed gases.

In some cases, many of the processes embodied in conventional steam cracker facilities share the same underlying principles of operation as those systems used in NGL processing or other processing facilities. For example, many of the separations systems, such as de-propanizer and/or de-ethanizer systems and C2 splitters, are typically included within cracker facilities to separate out unreacted components such as methane and ethane, or undesirable by-products from the olefin streams emanating from the cracker.

Figure 15:
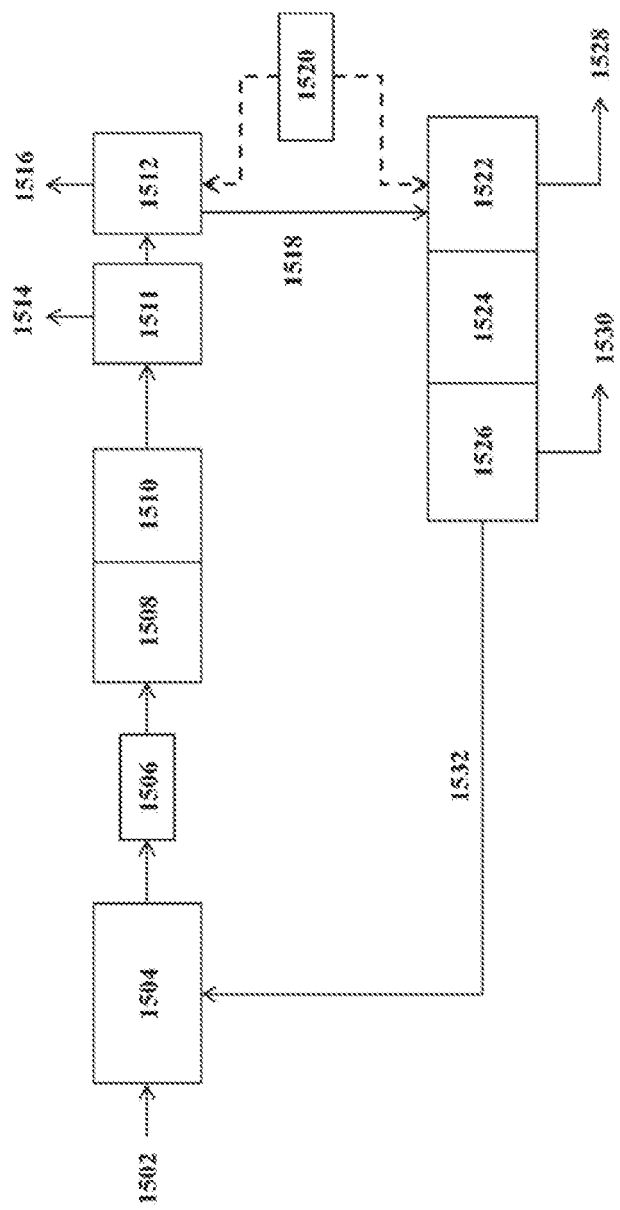
FIG. 15 schematically illustrates an example of the major unit operations of a steam cracking facility.

FIG. 15 shows a schematic illustration of an example of a steam cracker process and system. As shown, a feed gas stream 1502, such as naphtha, or ethane from an NGL processing facility described above, is delivered along with a steam feed (not shown), to the cracker's furnace 1504. Following cracking, the product is then quench cooled, e.g., in transfer line exchanger 1506. The resultant product gas is then passed through compression and treatment steps (1508 and 1510), that can include, for example, multistage gas compression, with each stage followed by cooling and liquid hydrocarbon and water removal, as well as gas treating for removal of acid gas components, e.g., $H_2S$ and $CO_2$, as well as dehydration to remove water, before being transferred to the cryogenic section (cold-box) 1511 for stage-wise cooling and condensation of various components, in order to remove CO and hydrogen in output 1514. The various liquid components are then fed to de-methanizer 1512 to separate out C1 compounds 1516, such as methane, from the higher hydrocarbons, e.g., $C_{2+}$ compounds in stream 1518. After de-methanizing, the $C_{2+}$ rich stream 1518 is then passed through further fractionation steps in e.g., de-ethanizer 1522, to separate the C2 components from higher hydrocarbons in stream 1528, an acetylene reactor 1524, to convert acetylene in the C2 rich stream to ethylene and ethane, and C2 splitter 1526 to separate ethylene from any residual ethane. The ethylene rich stream 1530 is then recovered as product, while the residual ethane recovered from the C2 splitter is recycled back through the cracker furnace 1504 in recycle stream 1532.

OCM Gas Processing Integration

OCM reactor systems and processes can be integrated into existing natural gas or other petrochemical processing facilities in one or more of a number of different specific points in such facilities, and with respect to a number of different inputs and outputs of either or both the OCM system and the unit processes of the overall processing facility. In particular, the OCM reactor systems can be integrated into conventional processing plants as one or both of a producer of feed streams for one or more processing units within the processing facility, and/or as a consumer of product streams from one or more processing units within the processing facility.

In some cases, integration includes a range of different integration types, including, e.g., process integration through fluid or gas coupling within a process stream. Fluid integration or fluid coupling or connection generally refers to a persistent fluid connection or fluid coupling between two systems within an overall system or facility. Such persistent fluid communication typically refers to an interconnected pipeline network coupling one system to another. Such interconnected pipelines may also include additional elements between two systems, such as control elements, e.g., heat exchangers, pumps, valves, compressors, turbo-expanders, sensors, as well as other fluid or gas transport and/or storage systems, e.g., piping, manifolds, storage vessels, and the like, but are generally entirely closed systems, as distinguished from two systems where materials are conveyed from one to another through any non-integrated component, e.g., railcar or truck transport, or systems not co-located in the same facility or immediately adjacent facilities. As used herein, fluid connection and/or fluid coupling includes complete fluid coupling, e.g., where all effluent from a given point such as an outlet of a reactor, is directed to the inlet of another unit with which the reactor is fluidly connected. Also included within such fluid connections or couplings are partial connections, e.g., were only a portion of the effluent from a given first unit is routed to a fluidly connected second unit. Further, although stated in terms of fluid connections, such connections include connections for conveying either or both of liquids and gas.

In some cases, integration refers to thermal or energy integration of, e.g., an OCM reactor system, into the energy infrastructure of a facility. Such integration may also include spatial integration of an OCM reactor system into the physical processing plant, e.g., "inside battery limits" (IBL), or it may be otherwise integrated, but outside battery limits (OBL) of the facility.

Figure 16:
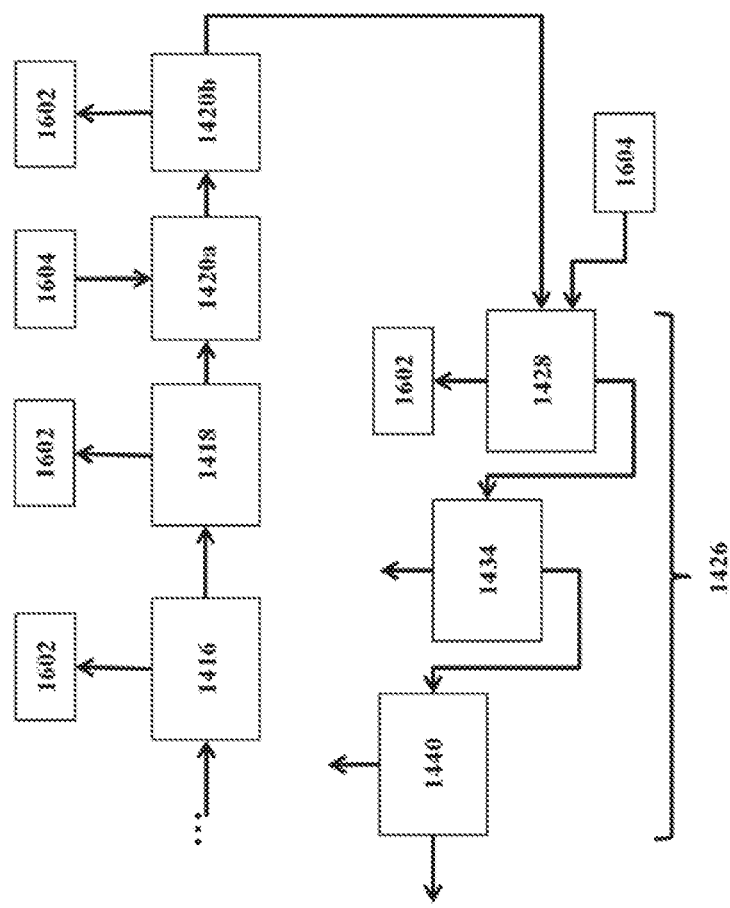
FIG. 16 presents a block diagram showing points where inputs and outputs of an OCM reactor system can integrate into a conventional natural gas processing system or facility.

FIG. 16 schematically illustrates a number of integration points for an OCM reactor system in the overall process path of a natural gas processing facility shown in FIG. 14. In particular, as shown in this example, an OCM input, schematically identified as block 1602, is shown integrated into and fluidly coupled at multiple points in the process stream, where the output or product of a particular processing unit is fed into the inlet of an OCM reactor system. For example, as shown, the OCM reactor is shown optionally fluidly coupled to the output of, e.g., dehydration unit 1416 or purification unit 1418, extraction unit 1420b, and de-ethanizer unit 1428.

Alternatively or additionally, the OCM reactor output, schematically illustrated as block 1604, is shown integrated, e.g., fluidly connected, with multiple points in the process stream where the OCM reactor product streams are fed into various processing units of the overall facility. By way of example, the OCM output 1604 may optionally be fluidly coupled to the inlet of the extraction unit 1420, fractionation train 1426, e.g., fractionation units 1428, 1434 or 1440, or further processing units (not shown).

Integration with OCM Gas Feed

In some embodiments, an OCM reactor system is connected downstream of one or more processing units in a gas processing facility whereby product streams from the processing unit are fed into the inlet stream of the OCM reactor system. In particular, processing units that include as one or more outputs, methane containing and/or methane rich streams, can provide feed gases to the OCM reactor system, for conversion of methane to higher hydrocarbons. Likewise, the outputs of the OCM system can generally provide feed streams to, and leverage the infrastructure of a number of systems in conventional processing units used to separate, modify and purify hydrocarbon mixtures.

In some cases, an OCM reactor system is provided integrated into an existing processing facility to take up at least a portion of the clean, dry pipeline ready natural gas for conversion of the methane contained in that gas, into higher hydrocarbons, instead of passing that portion of the dry gas through the extraction and fractionation units. In some cases, the inlet to the OCM reactor system can be fluidly coupled to the outlet of the acid gas removal unit 1408, dehydration unit 1416, or, as shown, additional purification unit 1418. As noted, this fluid connection may include one or more heat exchangers, pumps, compressors, or the like to present the dry gas to the OCM reactor system under conditions appropriate for initiation of the OCM catalytic reaction, e.g., inlet temperatures between 450° C. and 600° C., and pressures of 1 atmosphere or greater, and preferably, from about 15 pounds per square inch gauge (psig) to about 150 psig, 15 psig to about 125 psig, or less than 100 psig, or from about 15 psig to about 100 psig.

Alternatively or additionally, the OCM reactor system can be fluidly coupled to one or more outlets of the extraction unit(s) 1420, to route methane rich effluents from the extraction unit 1420 into the OCM reactor system for conversion of methane to ethylene and other hydrocarbons, which can be passed through the extraction unit to separate ethylene and other C2+ components from gas components, e.g., CO, $CO_2$, $N_2$ and unreacted methane. In some cases, these and other outputs of conventional processing facilities are beneficially exploited. For example, in some cases, $CO_2$ recovered from the OCM reactor products and separated in the extraction unit may be transported via pipeline or truck, used onsite, or otherwise beneficially used in enhanced oil recovery (EOR). Likewise, $N_2$ from the OCM reactor product and separated in the extraction unit is optionally recovered, and transported via pipeline or truck, used onsite, or otherwise beneficially used in, e.g., enhanced oil recovery (EOR). Similarly, $H_2O$ from the OCM reactor product that is separated in the OCM extraction or other purification units may be recovered and transported via pipeline or truck, used onsite, or otherwise beneficially used, e.g., as a fracking fluid.

In some cases, ethane rich streams from the fractionation train 1426, e.g., ethane rich effluent from de-ethanizer unit 1428, that may include small amounts of methane not previously removed, may be cycled into the OCM reactor, either alone, or in combination with one or more methane rich streams, to convert any residual methane in the OCM reactor to higher hydrocarbons. Further, as an intermediate in the OCM process, under the same reaction conditions of OCM, ethane present in the OCM feed may be reacted and converted into ethylene in the OCM reactor.

Ethane rich streams from the de-ethanizer may likewise be routed to ethane conversion systems. Such ethane conversion systems include, for example, steam cracking units that convert ethane to ethylene via non-oxidative dehydrogenation. In some cases, the ethane can be routed to additional reactor systems containing catalysts for oxidative dehydrogenation ("ODH") of ethane in the presence of an oxygen source, to produce ethylene. Catalysts and systems for carrying out ODH reactions are described in, for example, Cavani, et al., Catalysis Today (2007), Vol. 127 (1-4), 113-131, the full disclosure of which is incorporated herein by reference in its entirety for all purposes. Again, the outlet streams of either of these systems can be additionally recycled or routed as needed to other processing units within the facility.

Integration with OCM Product

In some embodiments, the OCM reactor system is provided upstream of one or more processing units in the gas processing facility, so that product streams from the OCM reactor system, referred to as "OCM product streams" or "OCM product gases", may be further processed by different processing units within the facility.

For example, an OCM reactor system product stream, that typically includes C2+ hydrocarbons, as well as potentially CO, $CO_2$, $N_2$ and unreacted methane and other products, is passed through the extraction unit 1420, such as a two stage cryogenic extraction unit 1420a and 1420b, to separate the ethylene, ethane, and other C3 through C5+ hydrocarbons, from the nitrogen, CO and $CO_2$ components, as well as any residual methane and other gas components. An example of a cryogenic extraction system for processing OCM product streams is described in U.S. patent application Ser. No. 13/739,954, filed Jan. 11, 2013, which is incorporated herein by reference in its entirety for all purposes. Briefly, cryogenic extraction systems typically include at least first and second separation units (e.g., separations units 1420a and 1420b), where the first unit (1420a) reduces the temperature of the incoming gas, e.g., NGL containing natural gas, or an OCM product gas. For purposes of discussion, the separations system is described in terms of an OCM Product gas. The first separations unit within a cryogenic separations system typically functions as a de-methanizer, as the reduction in temperature liquefies the $C_{2+}$ components to result in a bottoms portion that is $C_{2+}$ rich, while the remaining gas component, comprising mainly methane and $N_2$ components are removed from the top of the unit. This methane containing component is then passed through the second separations unit (1420b) which functions as a nitrogen rejection unit by liquefying the methane component and venting the nitrogen component.

Similarly, the OCM reactor system can also be provided fluidly coupled to a lean oil extraction unit for separation of the lighter hydrocarbon components from the other gas components.

In some cases, a product stream from the OCM reactor system, or optional oligomerization system, is optionally routed through the fractionation system, or one or more individual fractionation units of a conventional gas processing facility, to separate heavier hydrocarbons, e.g., $C_3$, $C_4$ or $C_5$+ hydrocarbons and NGLs, from the lighter hydrocarbons, e.g., ethane and ethylene. In such processes, the ethane can be pulled as a product or as noted elsewhere herein, redirected back into the OCM reactor system or to an ethane conversion process, e.g., as described above. In some cases, the OCM product can be routed through a full length fractionation system, e.g., multiple staged fractionation units, or may be routed through any individual or any subset of fractionation units in the overall fractionation system, e.g., just a de-ethanizer, or just a de-ethanizer and/or depropanizer, etc.

In some cases, the integration of the OCM reactor system in an upstream or downstream configuration as to one or more processing units within a gas processing facility, is not mutually exclusive, as in many cases, the OCM reactor will take inputs from and provide outputs to multiple different processing units in the processing facility, and in some cases will take inputs from and provide outputs to a single processing unit, e.g., a cryogenic extraction unit or a fractionation unit.

Figure 17:
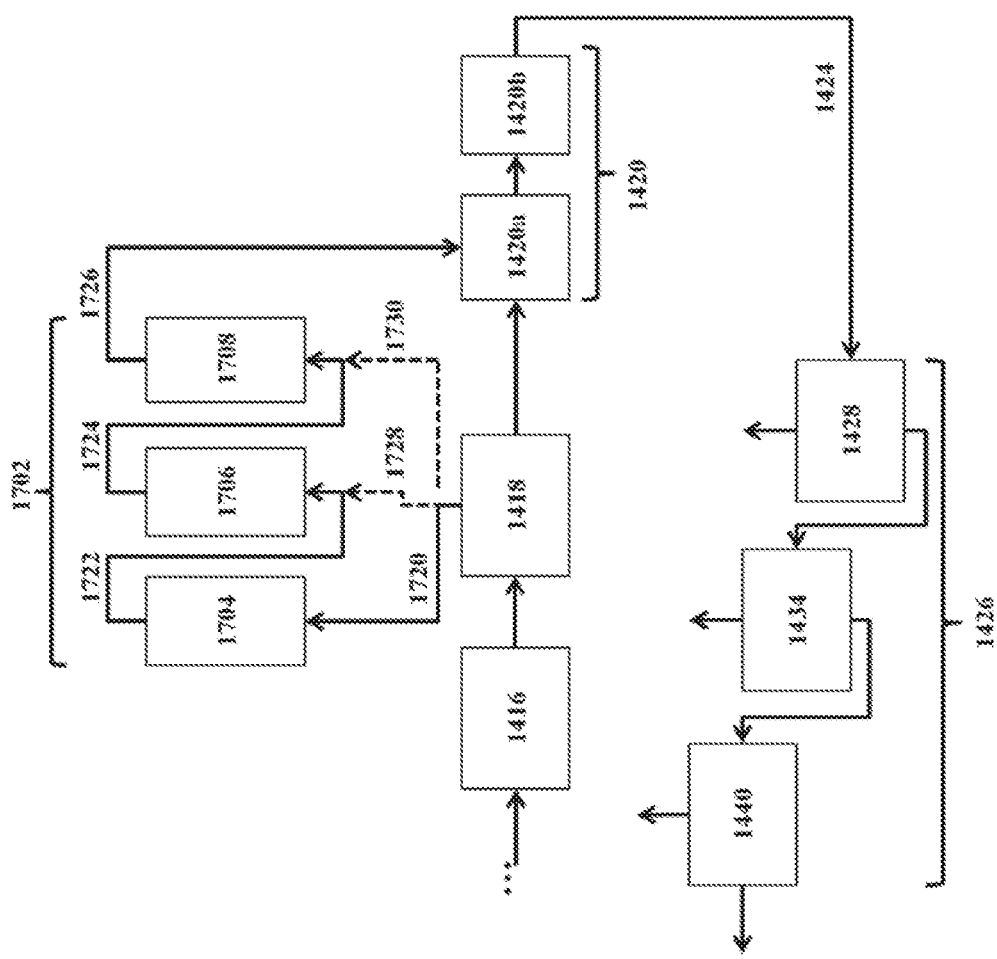
FIG. 17 presents a schematic illustration of an adiabatic OCM reactor system integrated into a first location in a natural gas processing facility.

FIG. 17 schematically illustrates one example of an OCM reactor system integrated into a conventional gas processing facility. In particular, shown is a staged adiabatic OCM reactor system 1702 coupled to the outlet of the purification unit 1418 of a gas facility. As shown, a clean, dry gas stream 1720 from purification unit 1418, which may be a portion or all of the output of the purification unit 1418 at a particular time, is routed to the inlet of first reactor 1704 of a staged adiabatic OCM reactor system 1702. The product stream 1722 from reactor 1704 is then, at least partially, introduced into the inlet of reactor 1706, whose product stream 1724, is at least partially introduced into the inlet of reactor 1708. While illustrated as a three-stage adiabatic reactor system 1702, it will be appreciated that two three, four or more stages may be employed in an adiabatic system. Such staged adiabatic systems are described in U.S. Provisional patent application Ser. No. 13/900,898, filed May 23, 2013, and incorporated herein by reference in its entirety for all purposes.

As shown, additional clean dry gas from purification unit 1418 may also be introduced into the subsequent reactors 1706 and 1708 in addition to the product stream of the preceding reactor, e.g., product streams 1722 and 1724, respectively, as shown by dashed arrows 1728 and 1730, to provide an additional source of methane for these subsequent reactors.

In addition to taking up at least a portion of the product stream from the purification unit(s) 1418 of the facility, the OCM product stream of the overall OCM reactor system, e.g., shown as the effluent stream 1726 from reactor 1708, may also be subjected to subsequent processing in the further processing units of the gas processing facility.

In particular, as shown in FIG. 17, the outlet of the OCM reactor system 1702 is fluidly coupled to the inlet of the extraction unit 1420 such that OCM product stream 1726 is introduced into the extraction unit 1420, to separate higher hydrocarbons, e.g., $C_2+$ components, in stream 1424, from any residual methane and nitrogen within the OCM product gas stream 1726, e.g., in the cryogenic demethanizing unit 1420a. These higher hydrocarbons are then optionally routed to the fractionation train 1426, e.g., units 1428, 1434 and 1440, for separation of the various different $C_2+$ constituents from the de-methanized product stream 1424. The fractionation unit is also referred to herein as a $C_2+$ fractionation unit. The methane and nitrogen containing components are then optionally routed through the nitrogen rejection unit, e.g., unit 1420b, to separate the nitrogen from the methane, which methane optionally may then be re-introduced into the OCM reactor system 1702 (not shown). As noted above, the cryogenic demethanizing unit, the entire cryogenic system 1420, or a similar separations unit may be positioned to receive the effluent gas from individual reactor stages, e.g., stages 1704 and 1706, as opposed to just receiving the final OCM reactor system product gas (stream 1726), in order to skim off $C_{2+}$ compounds from streams 1722 and 1724, respectively, while passing methane into the subsequent reactor stages for conversion. The resulting $C_{2+}$ containing streams would then be routed for subsequent processing, e.g., in fractionation train 1426. As noted, this would allow efficiencies in terms of reducing $C_2+$ product losses from stage to stage, as well as improving efficiencies of reactions based upon shifting equilibria, e.g., higher relative reactant concentration in each of the subsequent stages.

Figure 18:
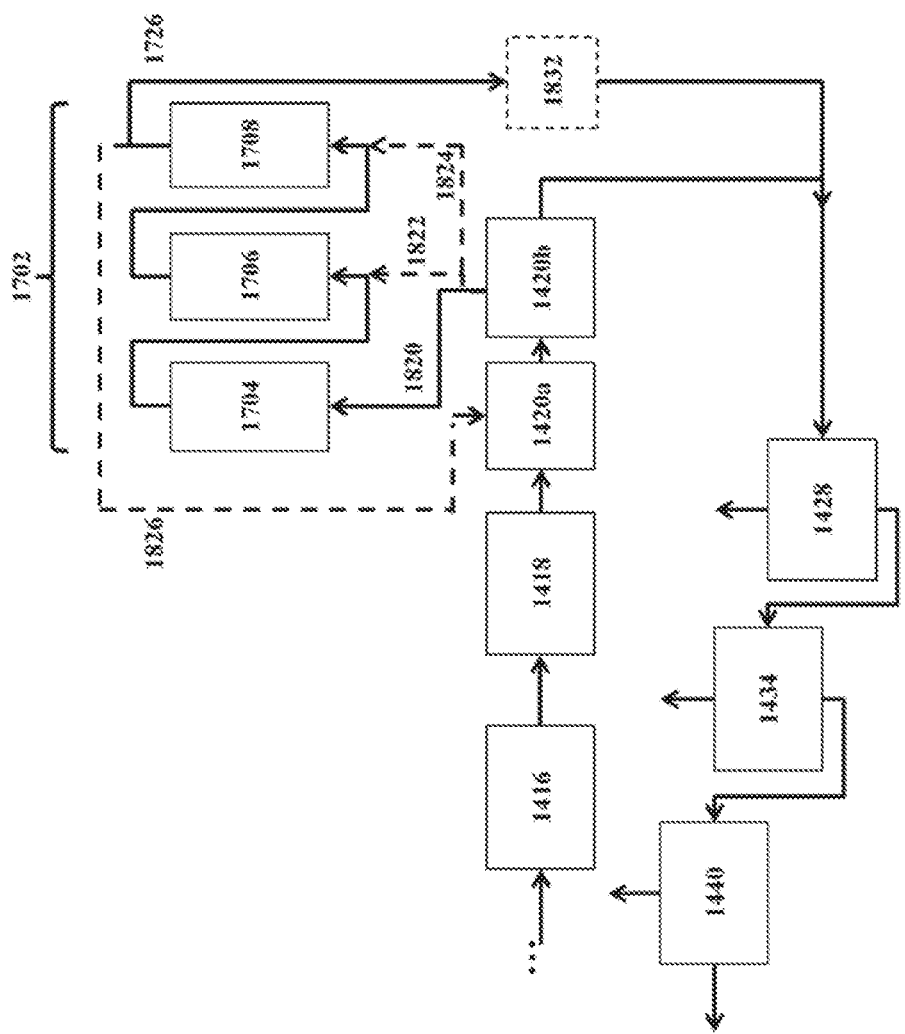
FIG. 18 provides a schematic illustration of an adiabatic OCM reactor system integrated into a second location in a natural gas processing facility.

FIG. 18 schematically illustrates an example of coupling of the OCM reactor system 1702 with the extraction unit 1420, and particularly, the cryogenic separation unit 1420b and the fractionation system, e.g., through de-ethanizer 1428. In particular, as shown, the methane rich gas effluent stream 1820 from the cryogenic extraction unit 1420b is introduced as a feed gas into the inlet of reactor 1704. As noted above, the product gas from the first staged reactor is, at least partially, fed into the subsequent reactors 1706 and 1708, along with optional additional methane containing gas feeds 1822 and 1824 from the outlet of cryogenic extraction unit 1420b. The product gas stream 1726 from the OCM reactor system 1702 is then fed into the fractionation train 1426 in order to separate out the various constituent $C_2+$ products. As shown, the OCM is optionally passed through optional oligomerization unit 1832, for conversion of $C_2+$ hydrocarbons, e.g., ethylene, to higher hydrocarbons, e.g., $C_3+$ hydrocarbons, which are then transferred to the fractionation system for separation of different higher hydrocarbons. Optionally the output of the oligomerization unit 1832 can be transferred to the fractionation system at various points, including but not limited to the input or output of units 1428, 1434, 1440.

Alternatively, or additionally, the product stream from the OCM reactor system is fed back through the extraction units 1420, as shown by the dashed line 1826 from the outlet of reactor 1708, in order to separate any residual methane and/or nitrogen from the desired OCM products, e.g., $C_2+$ products, as described above.

Alternatively, or additionally, the product stream from the oligomerization system is fed back through the extraction units 1420, in order to separate any residual methane and/or nitrogen from the desired oligomerization products, e.g., $C_2+$ products, as described above.

OCM—Cracker Integration

Figure 19:
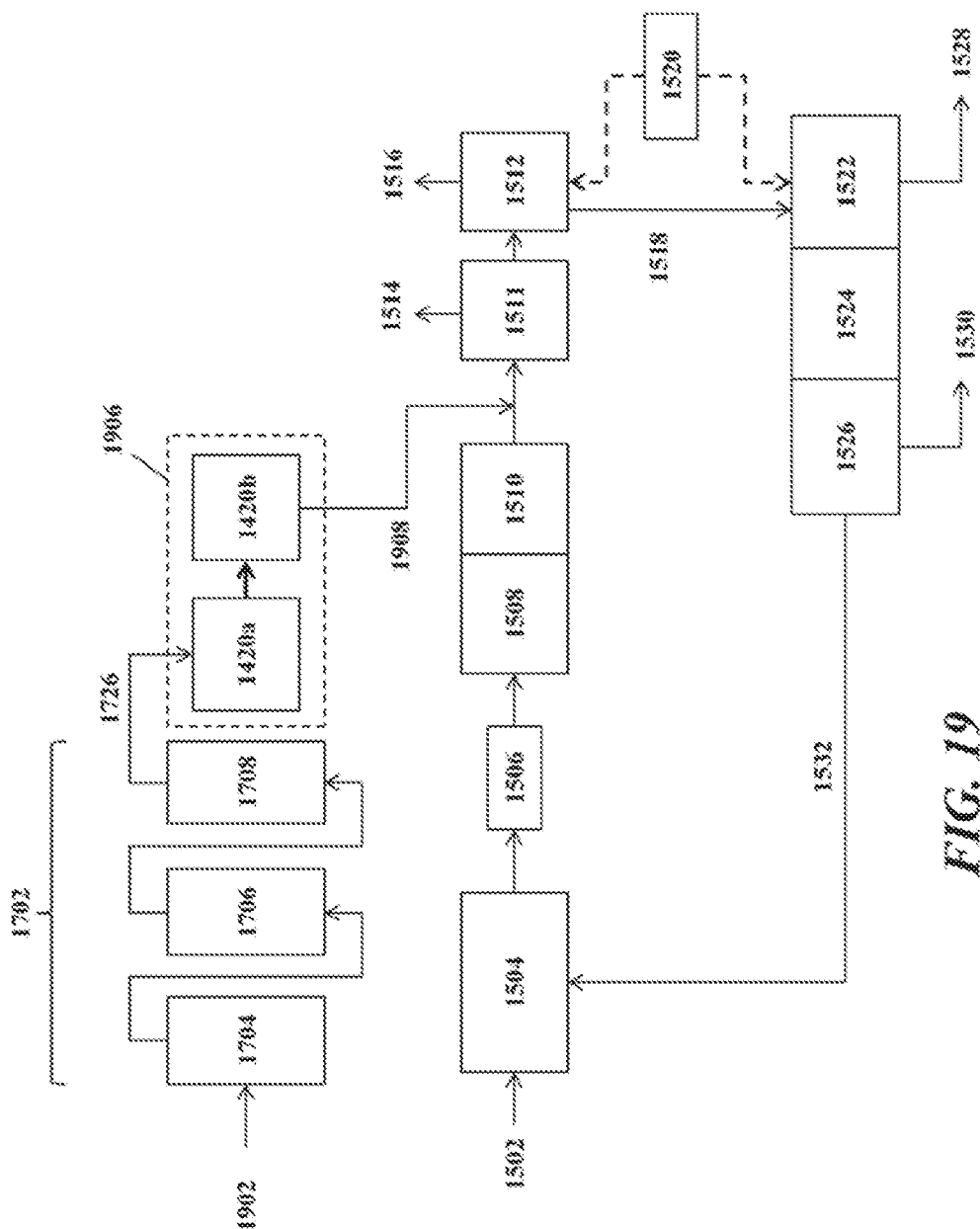
FIG. 19 provides a schematic illustration of an adiabatic OCM reactor system and cryogenic separation system integrated into a steam cracking facility.

As with natural gas processing facilities described above, substantial value can be derived from integration of OCM reactor systems into existing cracker facilities, such as ethane or naphtha crackers. FIG. 19 provides a schematic illustration of integration of an OCM system into a cracker facility. As shown in the simplified schematic of FIG. 15, a typical cracker unit, e.g., a naphtha cracker, includes the cracking furnace 1504 and closely associated quenching systems 1506. The $C_2+$ product gases from the cracker are then passed through appropriate treatment and compression systems 1508 and 1510, respectively, before routing to a coldbox and de-methanizer 1512 to separate out any residual methane and hydrogen present in the cracker effluent. The $C_2+$ stream 1518 is then routed through a separation or fractionation system that typically includes a de-ethanizer 1522 for separating the $C_2$ components from the higher hydrocarbons, e.g., $C_3+$, an acetylene converter 1524 that converts any acetylene produced during the cracking operation to ethylene, and a $C_2$ splitter 1526 for separating the ethylene (stream 1530) from the ethane (stream 1532) in the product gas, which is recycled back into the cracking furnace 1504.

In some cases, an OCM reactor system is integrated into a more conventional cracker facility to provide a number of benefits, including feedstock flexibility, product slate selectability, and energy efficiency.

An illustration of this integration is schematically shown in FIG. 19 for example. As shown, an OCM reactor system 1702 again includes one, two, three or more OCM reactors, such as staged adiabatic reactors 1704, 1706 and 1708, or one, two three or more serial or parallel isothermal reactors (not shown). In contrast to certain integrations within gas processing facilities, within a cracker process, the OCM reactor system may not share feedstock with the underlying facility. In particular, as noted above, the OCM reactor utilizes methane, and natural gas as its primary feedstock, e.g., in feed gas stream 1902, while the cracker's feedstock (stream 1502) will generally consist of ethane from NGLs, LPG, or naphtha. However, by providing an alternate source of ethylene, while relying upon many of the same unit operations for its production, an integrated OCM reactor system within a cracker facility provides significant advantages of feedstock flexibility. In particular, adverse fluctuations in feedstock price and/or availability of naphtha or ethane from NGLs can be partially, substantially, or completely mitigated through partial or substantial transition of a facility from a naphtha or ethane fed cracker facility to a methane fed OCM facility. In some instances, the methane feed for OCM can come from the methane produced from the steam cracking process which is typically burned to produce energy for the endothermic cracking process.

As shown, a methane containing feed gas 1902 typically including an oxidant gas component, e.g., air or enriched air, is delivered to the OCM reactor system 1702 and contacted with the OCM catalyst contained therein under OCM reaction conditions as described herein. As shown, the OCM product gas 1726, e.g., including ethylene, methane, ethane, and nitrogen, as well as other gases, such as CO and $CO_2$, is passed through a heat exchanger and compressor (not shown) before being passed into a cryogenic separation unit 1906 (including, e.g., cryogenic separation units 1420a and 1420b in FIG. 14) for separation of nitrogen, CO and $CO_2$, and removal of at least some of the residual methane present in the OCM gas. The $C_2$+ rich stream from the separation unit (stream 1908), containing ethylene, ethane, $C_3$+ hydrocarbons, as well as additional residual methane are then transferred to the downstream processing units of the cracker with which it is fluidly integrated, e.g., connected through a fluid coupling or connection. In particular, these product effluents from the cryogenic separation unit 1906 may be routed into, e.g., cold-box 1511 and de-methanizer 1512 for separation of any residual methane, as well as any remaining hydrogen, CO and $CO_2$. For this integration, the methane rejection in the demethanizer portion of the cryogenic unit associated with the OCM reactor, e.g., de-methanizing cryogenic unit 1420a, may preferably be tailored to be yield methane/$C_2$+ concentrations that are approximately equivalent to those concentrations for which the cracker demethanizer, e.g., demethanizer 1512, is configured to address. As a result of reliance upon the cracker's existing demethanization capacity, the cryogenic separation unit associated with the OCM reactor, e.g., cryo unit 1906, is unloaded, and may be provided with a correspondingly reduced capacity, yielding significant capital savings. In some cases, a similar approach may be employed in the gas processing facility implementation described above. In particular, and with reference to FIG. 17, an additional demethanization operation can be included in stream 1726, so as to be substantially equivalent to the methane content of the OCM output with the operating methane load of the facility's existing extraction unit, e.g., unit 1420. In both the cracker and gas processing implementation, this results in a substantial reduction in capital expense, as it permits lower cost operations to integrate into the existing higher cost separations operations.

The $C_{2+}$ products can then be routed into the cracker's fractionation train, e.g., de-ethanizer 1522, acetylene reactor 1524 and $C_2$ splitter 1526, to recover ethylene and recycle ethane back into the cracker furnace 1504.

In addition to providing feedstock flexibility to a cracker facility, an integrated OCM reactor system can also provide flexibility in selection of product slates, by allowing for a relaxation in the operating severity of the cracker process. In particular, the ratio of ethylene to co-products, e.g., propylene, etc., in a cracker process is a function of the cracking severity, which can be a function of the reaction conditions. Because the highest demand is generally for ethylene, crackers tend to be operated to maximize ethylene production and minimize co-products, typically with an ethylene to propylene ratio of, e.g., greater than 2, using a naphtha feedstock. However, by supplementing ethylene production through the use of the integrated OCM reactor system, one can adjust the severity of the cracking process, e.g., to an ethylene to propylene ratio of less than 2, less than or equal to about 1.5, less than or equal to 1.25, less than or equal to 1, or less, using the naphtha feedstock, to produce greater amounts of co-products as may be economically prudent given then current market conditions. Product slate optimization can be particularly useful in a naphtha cracker environment where the co-product production is more meaningful than in an ethane cracking environment, where no significant co-products are generally produced.

In some cases, a cracker facility is supplemented using an integrated OCM reactor system in the amount of greater than about 5% of the ethylene produced on a weight for weight basis, greater than about 10% of the ethylene produced, on a weight for weight basis. In some cases, a cracker facility is supplemented using an integrated OCM reactor system in the amount of at least about 20%, at least about 30%, and in some cases greater than about 40% or even 50%. In some embodiments, at least 2%, at least 5%, at least 10%, at least 20%, at least 30%, at least 40%, or at least 50% of the ethylene produced by the integrated facility is produced directly from the OCM reactor portion.

In some embodiments, the contribution of the integrated OCM system, calculated on a weight for weight basis when including as ethylene produced from OCM as the total ethylene produced from the OCM reactor's feedstock (i.e., including both the ethylene produced directly from the OCM reaction, as well as ethylene from cracked ethane that is produced by the OCM reactors), is between about 10% and about 50%, between about 20% and about 50%, between about 30% and about 50%, or between about 40% and about 50%.

In some embodiments, in order to provide even further product flexibility, the OCM effluent can be optionally routed into an ethylene oligomerization unit (either adiabatic or isothermal reactors described previously) that is designed to output a narrow band of aromatic hydrocarbons, e.g., benzene, toluene and xylene (BTX) or benzene, toluene, ethylbenzene, and xylenes (BTEX), for a portion of the OCM output stream. In conjunction with the above described operational flexibility, this configuration can specifically provide the ability to change the severity of the cracking units in combination with the OCM unit and the optional ethylene oligomerization unit to output the desired mix of ethylene, propylene, C4 and C5 olefins, and provide additional flexibility on the selection of product slates of the overall system to produce greater amounts of high value aromatic compounds.

Energy Integration

Heat, electricity, mechanical work, or any other form of energy can be transferred between the processes described herein (e.g., OCM, ODH) and hydrocarbon or other processes (e.g., non-OCM processes such as refineries, natural gas processing facilities, crackers). The energy can be transferred to the OCM process or from the OCM process at any suitable point and in any suitable manner (e.g., using a heat exchanger).

In addition to integration of the OCM reactor feeds and products into conventional hydrocarbon processing facilities, e.g., natural gas processing facilities, refineries, crackers, etc., or their component units or systems, also provided herein is energy integration of the OCM process into existing systems. In particular, by exploiting the thermal energy produced in the highly exothermic OCM reaction, one can augment the thermal systems of an existing facility, e.g., heaters and boilers, to potentially reduce the overall energy that is needed to be separately generated for control of the other processing units in the facility.

As noted above, OCM is a highly exothermic reaction that, under some circumstances, operates at temperatures between about 400° C. and 950° C., depending upon the reactor process and system used, and in any event at reactor feed inlet temperatures of between about 400° C. and 600° C. Accordingly, initiation of the OCM reaction tends to require an initial input of thermal energy to elevate the reactants and catalysts to an appropriate reaction initiation, or "light off" temperature. Once initiated, the exothermic nature of the reaction typically produces sufficient thermal energy to maintain the reaction. Additionally, as the OCM catalytic process tends to generate thermal energy, it can become necessary to remove thermal energy from one or more of the reactor systems and/or the product gas streams, in order to efficiently manage the catalytic reaction and subsequent processing steps. In some cases, this excess of thermal energy can be used as one or both of a thermal and other energy source for other facility operations. In some configurations, overall reaction temperatures can span from light off temperatures of between 400° C. to 600° C., to maximum reactor outlet temperatures of upwards of 950° C., depending upon whether the reactor system is operated in an isothermal or adiabatic configuration.

In some cases, and with reference to, e.g., a natural gas fractionation facility, thermal energy created by the OCM reaction can be removed from OCM product gas streams, or in the case of isothermal reactor systems, other heat exchange media, to heat different components of the fractionation unit, e.g., the de-ethanizer, etc. In other words, rather than separately generating thermal energy to drive process aspects of a processing facility, the OCM reactor system provides some or all of that thermal energy. This provides an additional value add from the OCM reactor system, on top of the generation of highly valuable hydrocarbon products.

Figure 20:
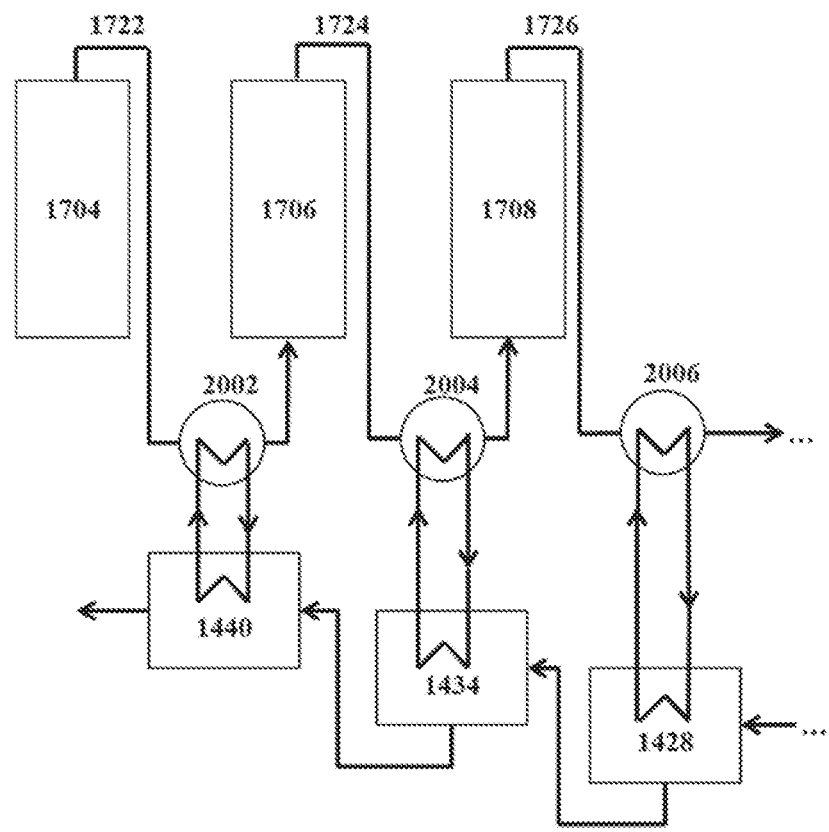
FIG. 20 provides a schematic illustration of integration of thermal energy systems from an OCM reactor system into thermal management processes for other processing systems within a natural gas processing facility.

For example, with reference to the process illustrated in FIG. 20, OCM product gas streams, e.g., intermediate OCM product streams 1722 and/or 1724, and/or final OCM product stream 1726, may be passed through one or more heat exchangers, e.g., heat exchangers 2002 and 2004, to reduce the temperature of the OCM product gas to temperatures appropriate for introduction into the subsequent reactors 1706 and 1708, respectively. Likewise, OCM product gas stream 1726 may be passed through heat exchanger 2006, to reduce the temperature of that stream to levels appropriate for the subsequent processing steps. Steam, water or any other heat exchange medium that is run through heat exchangers 2002, 2004 and/or 2006 is routed through one or more of de-ethanizer 1428, de-propanizer 1434 and/or debutanizer 1440, to provide thermal energy used in boiling off components in the fractionation process. This thermal energy may be used alone or to supplement the existing boiler capacity of a processing facility, and reduce the amount of energy required for that boiler capacity.

Additionally, thermal energy removed from the OCM reactor system or product streams may also be used to heat other process streams in the facility. For example, in addition to being used to heat the feed stream of the OCM reactor system to appropriate catalytic temperatures, the thermal energy from the OCM product streams or reactor systems may be used to heat cooled NGL streams following cryogenic extraction of those NGLs from the natural gas stream or the OCM reactor gas output. This is schematically illustrated in FIG. 20.

In some cases, in using thermal transfer between the cooled NGL stream from the cryogenic extractor, one is simultaneously heating the NGL stream, while cooling the heat exchange medium that is used to cool the OCM product streams.

Alternatively, or additionally, thermal energy removed from the OCM system can be converted to electrical energy. For example, product gases, or in the case of isothermal reactors, a heat exchange medium that is carrying heat away from a reactor itself, may be passed through a heat exchanger to create steam which is used to drive the turbine of a electrical generator. The resulting electrical energy can then be used to augment the power used for operating additional systems of the facility, such as lighting, office systems, pumps, and other control systems. In such cases, the electrical generation system constitutes a processing unit, for the energy integration of the OCM reactors into the processing plant. In particular, thermal energy from the OCM reactor system is conveyed to the electrical generator to generate electricity from steam, which electrical energy is, in turn, conveyed to one or more different processing units within the plant, or to other operations within the plant, even back out to the electrical grid.

As noted above with respect to feed and product integration of OCM reactor systems in a gas processing facility or system, OCM reactor systems may have multipoint integration into a gas processing system in terms of feed, product, thermal energy and electrical energy, and may, in some cases be integrated as to most or all of the foregoing aspects. For example, OCM reactor feed may derive from the effluent of an extraction unit, while the product of the OCM reactor system may be fed to the extraction unit of the overall facility. Thermal energy derived from the exothermic OCM reactor system may concurrently be used to augment boiler capacity used to operate the fractionation systems and or heat the feed gases used in the OCM reactor system. Further, excess steam generation from the exothermic OCM reactor system may concurrently be used in electricity generation using a conventional steam electric generator system. Any combination of multipoint integration can be practiced.

As with the NGL processing facilities described above, energy conservation and re-use can also be applicable to cracker facilities for the purposes of "on-purpose" steam generation, e.g., for driving turbines, boilers, compressors, etc. In particular, heat generated by the OCM reactor systems may be used to supplement or supplant the boilers typically used in cracker operations. Likewise, cooled streams or heat exchange media, may be circulated through heat exchangers in the OCM reactor system, to cool effluents from that system. Further, heat energy may again be converted to electrical energy, as described above.

In some cases, the integrated systems may be used in the generation and collection of carbon dioxide for use in still other natural gas processes. In particular, bulk carbon dioxide has found recycle uses in the oil and gas industry in, for example, enhanced oil recovery ("EOR") processes. In EOR processes, $CO_2$ is injected into oil reservoirs to displace oil from porous rock, as well as provide reduced viscosity.

Carbon dioxide ($CO_2$) generated as a by-product in an OCM reaction can be separated in an extraction process. Rather than being discarded, however, the $CO_2$ can be collected for use. The collected $CO_2$ may be stored on-site at the facility or it may be transported to a site where it will be used, such as an oil field. Such transportation may involve truck, train or pipeline transport, depending upon the amount of $CO_2$ involved. In addition to using a 'waste' product from the overall system for a useful end, the beneficial use of $CO_2$ can also provide gas facility operators with carbon credits for sale or trade with other producers of greenhouse gases. These credits can provide additional value to facility operators from the integrated OCM systems described herein.

Using Un-Reacted Methane as Fuel in Hydrocarbons Process

OCM reactions are generally not performed with complete conversion (e.g., not all of the methane that enters the OCM reactor is converted to $C_{2+}$ hydrocarbons). Un-reacted methane can be recycled back to the OCM reactor in some cases (e.g., following a separation). Another use for the un-reacted methane disclosed herein is to combust the methane in a hydrocarbon process (i.e., to provide energy).

In an aspect, a method for integrating an oxidative coupling of methane (OCM) process with a hydrocarbon process comprises providing an OCM product stream comprising $C_{2+}$ hydrocarbons and un-reacted methane, performing a separation that provides a first stream enriched in methane and provides a second stream enriched in $C_{2+}$ hydrocarbons, and combusting the first stream to provide energy for the hydrocarbon process. The hydrocarbon process can be without limitation an oil refinery, a natural gas liquids (NGL) process, or a cracker.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents. It is intended that the following claims define the scope of the invention and that methods and structures within the scope of these claims and their equivalents be covered thereby.

What is claimed is:

1. A method of producing hydrocarbons having two or more carbon atoms ($C_{2+}$), the method comprising:
   (a) directing a first feed stream comprising methane into an oxidative coupling of methane (OCM) reactor, wherein the OCM reactor is configured to generate $C_{2+}$ compounds from said methane;
   (b) performing one or more OCM reactions in the OCM reactor using said methane to produce a first product stream comprising one or more $C_{2+}$ compounds;
   (c) directing a second feed stream comprising saturated hydrocarbons to a steam cracker to produce a second product stream comprising unsaturated hydrocarbons including ethylene and propylene, wherein a ratio of ethylene to propylene is less than 2:1; and
   (d) directing at least a portion of said first product stream and said second product stream to an integrated fractionation system to produce one or more hydrocarbon streams comprising a $C_{2+}$ compound.

2. The method of claim 1, further comprising drying said first product stream prior to step (d).

3. The method of claim 1, further comprising: prior to step (d), subjecting said first product stream to pressure swing adsorption (PSA) to generate at least a first stream and a second stream, wherein said first stream has a lower concentration of $C_{2+}$ compounds than said second stream; and directing said second stream to the integrated fractionation system.

4. The method of claim 3, wherein said first stream comprises methane and impurities.

5. The method of claim 4, further comprising: separating said first stream to generate a methane stream and an impurities stream.

6. The method of claim 5, further comprising: directing at least a portion of said methane stream to said OCM reactor.

7. The method of claim 4, wherein the impurities comprise argon (Ar), hydrogen ($H_2$), carbon monoxide (CO), carbon dioxide ($CO_2$), nitrogen ($N_2$), or any combination thereof.

8. The method of claim 4, wherein at least 95% of the impurities are removed in the PSA.

9. The method of claim 1, wherein said one or more $C_{2+}$ compounds are hydrocarbons having from two to five carbon atoms.

10. The method of claim 1, wherein the $C_{2+}$ compounds comprise ethylene.

11. The method of claim 3, wherein said PSA comprises:
    (a) introducing said first product stream comprising said one or more $C_{2+}$ compounds and non-$C_{2+}$ impurities into a vessel at a first pressure, wherein the vessel comprises an adsorbent medium, wherein upon introducing said first product stream into said vessel said first product stream is brought into contact with said adsorbent medium; and
    (b) changing the pressure in the vessel to a second pressure to release (i) at least a subset of said one or more $C_{2+}$ compounds or (ii) said non-$C_{2+}$ impurities from said adsorbent medium, thereby separating the first product stream into at least a first stream comprising said non-$C_{2+}$ impurities and a second stream comprising at least the subset of said one or more $C_{2+}$ compounds.

12. The method of claim 11, wherein the second pressure is greater than the first pressure.

13. The method of claim 11, wherein the second pressure is less than the first pressure.

\* \* \* \* \*